United States Patent
De Ridder

(10) Patent No.: US 8,364,271 B2
(45) Date of Patent: Jan. 29, 2013

(54) ELECTRICAL STIMULATION SYSTEM AND METHOD FOR STIMULATING TISSUE IN THE BRAIN TO TREAT A NEUROLOGICAL CONDITION

(75) Inventor: Dirk De Ridder, Zelzate (BE)

(73) Assignee: Advanced Neuromodulation Systems, Inc., Plano, TX (US)

( * ) Notice: Subject to any disclaimer, the term of this patent is extended or adjusted under 35 U.S.C. 154(b) by 386 days.

(21) Appl. No.: 12/503,627

(22) Filed: Jul. 15, 2009

(65) Prior Publication Data

US 2009/0287274 A1 Nov. 19, 2009

Related U.S. Application Data

(63) Continuation of application No. 11/078,114, filed on Mar. 11, 2005, now abandoned.

(60) Provisional application No. 60/552,674, filed on Mar. 11, 2004.

(51) Int. Cl.
*A61N 1/18* (2006.01)

(52) U.S. Cl. ............ 607/45; 607/62; 607/139; 600/383; 600/378; 600/544; 600/13

(58) Field of Classification Search .................... 607/45, 607/62, 139; 600/383, 378, 544, 13
See application file for complete search history.

(56) References Cited

U.S. PATENT DOCUMENTS

| | | | |
|---|---|---|---|
| 4,844,075 A | 7/1989 | Liss et al. | |
| 5,697,975 A | 12/1997 | Howard et al. | |
| 5,938,688 A | 8/1999 | Schiff | |
| 6,167,311 A * | 12/2000 | Rezai | 607/45 |
| 6,198,958 B1 | 3/2001 | Ives et al. | |
| 6,266,556 B1 * | 7/2001 | Ives et al. | 600/544 |
| 6,295,472 B1 | 9/2001 | Rubinstein et al. | |
| 6,418,344 B1 | 7/2002 | Rezai et al. | |
| 6,463,328 B1 | 10/2002 | John | |
| 6,539,263 B1 | 3/2003 | Schiff et al. | |
| 6,959,215 B2 | 10/2005 | Gliner et al. | |
| 2002/0087201 A1 * | 7/2002 | Firlik et al. | 607/45 |
| 2003/0074032 A1 * | 4/2003 | Gliner | 607/45 |
| 2003/0125786 A1 | 7/2003 | Gliner et al. | |
| 2003/0135248 A1 | 7/2003 | Stypulkowski et al. | |
| 2005/0113882 A1 | 5/2005 | Cameron et al. | |
| 2006/0004422 A1 | 1/2006 | De Ridder | |
| 2006/0069415 A1 | 3/2006 | Cameron et al. | |

OTHER PUBLICATIONS

Brown, et al., "Motor cortex stimulation for central and neuropathic pain: current status," Pain, 104(3): 431-5, 2003.
Bruehlmeier, et al., "How does the human brain deal with a spinal cord injury?" Eur. J. Neurosci., 10(12): 3918-22, 1998.
Condes-Lara, et al., "Brain somatic representation of phantom and intact limb: a fMRI study case report," Eur. J. Pain, 4(3): 239-45, 2000.
De Ridder, et al., "Magnetic and electrical stimulation of the auditory cortex for intractable tinnitus," J. Neurosurg., 100: 560-564, 2004.

(Continued)

*Primary Examiner* — Carl H Layno
*Assistant Examiner* — Natasha Patel
(74) *Attorney, Agent, or Firm* — Christopher S. L. Crawford; Craig Hoersten

(57) ABSTRACT

According to one aspect, a stimulation system is provided for electrically stimulating a predetermined site to treat a neurological condition. The system includes an electrical stimulation lead adapted for implantation in communication with a predetermined site, wherein the site is brain tissue site. The stimulation lead includes one or more stimulation electrodes adapted to be positioned in the predetermined site. The system also includes a stimulation source that generates the stimulation pulses for transmission to the one or more stimulation electrodes of the stimulation lead to deliver the stimulation pulses to the predetermined site to treat a neurological disorder or condition.

2 Claims, 8 Drawing Sheets

OTHER PUBLICATIONS

Doetsch, et al., "Short-term plasticity in primary somatosensory cortex of the rat: rapid changes in magnitudes and latencies of neuronal responses following digit denervation," Exp. Brain Res., 112(3): 505-12, 1996.

Flor, et al., "Phantom-limb pain as a perceptual correlate of cortical reorganization following arm amputation," Nature, 375(6531): 482-4, 1995.

Flor, "Cortical reorganisation and chronic pain: implications for rehabilitation," J. Rehabil. Med., 41 Suppl: 66-72, 2003.

Halbert, et al., "Evidence for the optimal management of acute and chronic phantom pain: a systematic review," Clin. J. Pain, 18(2): 84-92, 2002.

Jastreboff, "Phantom auditory perception (tinnitus): mechanisms of generation and perception," Neurosci. Res., 8(4): 221-54, 1990.

Kaas, et al., "The reorganization of somatosensory cortex following peripheral nerve damage in adult and developing mammals," Annu. Rev. Neurosci., 6: 325-56, 1983.

Katayama, et al., "Motor cortex stimulation for phantom limb pain: comprehensive therapy with spinal cord and thalmic stimulation," Stereotact. Funct. Neurosurg., 77(1-4): 159-62, 2001.

Kandel, "Cellular mechanisms of hearing and the biological basis of individuality," Principles of Neural Science, $3^{rd}$ ed., Appleton & Lange Norwalk, Connecticut, 1009-1031, 1991.

Knecht, et al., "Plasticity of plasticity? Changes in the pattern of perceptual correlates of reorganization after amputation," Brain, 121:717-724, 1998.

Kumar, et al., "Deep Brain Stimulation for Intractable Pain: a 15-Year Experience," Neurosurgery, 40(4): 736-747, 1997.

Lende, et al., "Relief of facial pain after combined removal of precentral and postcentral cortex," J. Neurosurg., 34(4): 537-43, 1971.

Lenz, et al., "Characteristics of the bursting pattern of action potentials that occurs in the thalamus of patients with central pain," Brain Res., 496(1-2): 357-60, 1989.

Levy, et al., "Treatment of Chronic Pain by Deep Brain Stimulation: Long Term Follow-up and Review of the Literature," Neurosurgery, 21(6): 885-893, 1987.

Lotze, et al., "Phantom movements and pain: An fMRI study in upper limb amputees," Brain, 124: 2268-2277, 2001.

Merzenich, et al., "Somatosensory cortical map changes following digit amputation in adult monkeys," J. Comp. Neurol. 224(4): 591-605, 1984.

Moller, "Similarities between chronic pain and tinnitus," Am. J. Otol., 18(5): 577-85, 1997.

Nguyen, et al., "Treatment of deafferentation pain by chronic stimulation of the motor cortex: report of a series of 20 cases," Acta Neurochir. Suppl., 68: 54-60, 1997.

Nikolajsen, et al., "Phantom limb pain,"Br. J. Anaesth., 87(1): 107-16, 2001.

Peyron, et al., "Functional imaging of brain responses to pain. A review and meta-analysis," Neurophysiol. Clin., 30(5): 263-88, 2000.

Pons, et al., "Massive cortical reorganization after sensory deafferentation in adult macaques," Science, 252(5014): 1857-60, 1991.

Ramachandran, et al., "Behavioral and magnetoencephalographic correlates of plasticity in the adult human brain,"Proc. Natl. Acad. Sci. USA, 90: 10413-10420, 1993.

Ramachandran, et al., The perception of phantom limbs, Brain, 121: 1603-1630, 1998.

Rinaldi, et al., Spontaneous neuronal hyperactivity in the medial and intralaminar thalmic nuclei of patients with deafferention pain, J. Neurosurg., 74(3): 415-21, 1991.

Sherman, et al., "Chronic phantom and stump pain among American veterans: results of a survey," Pain, 18(1): 83-95, 1984.

Theuvenet et al., "Responses to median and tibial nerve stimulation in patients with chronic neuropathic pain," Brain Topogr., 11(4): 305-13, 1999.

Tonndorf, "The analogy between tinnitus and pain: a suggestion for a physiological basis of chronic tinnitus," Hear. Res., 28(2-3): 271-5, 1987.

Tsubokawa, et al., "Chronic Motor Cortex Stimulation for the Treatment of Central Pain," Acta Neurochirurgica, Suppl. 52: 137-139, 1991.

Tsubokawa, et al., "Treatment of Thalamic Pain by Chronic Motor Cortex Stimulation," Pacing Clin. Electrophysiol., 14: 131-134, 1991.

Weiss, et al., "Rapid functional plasticity of the somatosensory cortex after finger amputation," Exp. Brain Res., 134(2): 199-203, 2000.

Yuste, et al., "Development and plasticity of the cerebral cortex: from molecules to maps," J. Neurobiol., 41(1): 1-6, 1999.

USPTO, Office Action for U.S. Appl. No. 12/353,340 dated Aug. 19, 2010.

* cited by examiner

ELECTRICAL STIMULATION SYSTEM AND METHOD FOR STIMULATING TISSUE IN THE BRAIN TO TREAT A NEUROLOGICAL CONDITION

CROSS-REFERENCE TO RELATED APPLICATIONS

This application is a continuation of U.S. application Ser. No. 11/078,114, filed Mar. 11, 2005, now abandoned, which claims the benefit of U.S. Provisional Application No. 60/552,674, filed Mar. 11, 2004, which is incorporated herein by reference.

TECHNICAL FIELD

This invention relates generally to electrical stimulation of a person's brain and in particular to an electrical stimulation system and method for stimulating tissue in the brain to treat a neurological condition, for example pain.

BACKGROUND OF THE INVENTION

Many people experience adverse conditions associated with functions of the cortex, the thalamus, and other brain structures. Such conditions have been treated effectively by delivering electrical energy to one or more target areas of the brain. One method of delivering electrical energy to the brain involves inserting an electrical stimulation lead through a burr hole formed in the skull and then positioning the lead in a precise location proximate a target area of the brain to be stimulated such that stimulation of the target area causes a desired clinical effect. For example, one desired clinical effect may be cessation of tremor from a movement disorder such as Parkinson's Disease. A variety of other clinical conditions may also be treated with deep brain stimulation, such as essential tremor, tremor from multiple sclerosis or brain injury, or dystonia or other movement disorders. The electrical stimulation lead implanted in the brain is connected to an electrical signal generator implanted at a separate site in the body, such as in the upper chest.

Chronic pain afflicts approximately 86 million Americans and it is estimated that United States business and industry loses about $90 billion dollars annually to sick time, reduced productivity, and direct medical and other benefit costs due to chronic pain among employees. Because of the staggering number of people affected by chronic pain, a number of therapies have been developed that attempt to alleviate the symptoms of this condition. Such therapies include narcotics, non-narcotics, analgesics, antidepressants, anticonvulsants, physical therapy, biofeedback, transcutaneous electrical nerve stimulation (TENS), as well as less conventional or alternative therapies. Other treatment options involve neuroaugmentive techniques such as spinal cord stimulation or intrathecal pumps. For a subset of patients, however, these therapies are inefficacious and more invasive procedures such as blocks, neurolysis and ablative procedures become the only options for treatment. In particular, ablative procedures, although infrequently utilized, are the primary alternative for patients unresponsive to other modes of treatment. Such procedures, however, have the fundamental limitation of being inherently irreversible and being essentially a "one-shot" procedure with little chance of alleviating or preventing potential side effects. In addition, there is a limited possibility to provide continuous benefits as the pathophysiology underlying the chronic pain progresses and the patient's symptoms evolve. Because of the inherent disadvantages of ablative procedures, electrical stimulation of the brain has become an attractive neurosurgical alternative to alleviate the symptoms of chronic pain.

Electrical stimulation of the brain for chronic pain has been used since the 1950s when temporary electrodes were implanted in the septal region for psychosurgery in patients with schizophrenia and metastatic carcinoma. In particular, electrodes were placed in the septum pellucidum in a region anterior and inferior to the foramen of Monro. In the in six patients with intractable pain, but successful pain relief was obtained in only one patient. Despite these earlier reports of septal and caudate stimulation, current applications of electrical stimulation for pain involve thalamic, medial lemniscus, internal capsule stimulation, periventricular gray and pariaqueductal gray stimulation. For example, thalamic stimulation for pain relief was first reported for stimulation along the ventroposterolateral nucleus and ventralis posterior to relieve chronic intractable deafferentation pain and stimulation along the ventroposteromedial nucleus to relieve refractory facial pain. With respect to internal capsule stimulation, chronic stimulating electrodes have been implanted in the posterior limb of the internal capsule in a number of patients, including patients with lower-extremity pain and spasticity following spinal cord injury.

Although the above-mentioned target sites are all deep brain stimulation target sites, several studies have supported the role of motor cortex stimulation for pain control. For example, in the process of performing sensory cortex stimulation in an attempt to relieve thalamic pain, it was found that stimulation of the precentral gyrus/motor cortex was effective in relieving thalamic pain. Interestingly, stimulation of the sensory cortex exacerbated the pain in many patients.

Therefore, despite previous attempts to alleviate the symptoms of chronic pain by deep brain or cortical stimulation, there is still an unmet need for a method of treating chronic pain that is effective in a larger subset of the patient population.

BRIEF SUMMARY OF THE INVENTION

The electrical stimulation system and method of the present invention may reduce or eliminate certain problems and disadvantages associated with previous techniques for treating neurological conditions, such as pain, for example.

According to one embodiment, an electrical stimulation system is provided for electrically stimulating target tissue in a person's brain to treat a neurological condition. The system includes an electrode adapted for implantation into a person's skull for electrical stimulation of target tissue in the person's brain. The system also includes a pulse generating source operable to generate electrical stimulation pulses for transmission to the electrodes to deliver the electrical stimulation Dulses to the target tissue in the brain to adjust the level of activity in the target tissue in the brain to treat the neurological condition.

The target tissue can be a cortical tissue site, for example the somatosensory cortex or sensory cortex. The somatosensory cortex includes, but is not limited to the primary somatosensory cortex, the secondary somatosensory cortex, and the somatosensory association complex. Yet further, the target tissue can be identified by mapping the person's brain. Mapping a person's or subject's brain provides information to identify areas of the brain that exhibit altered neuronal activity, such as increased or decreased neuronal activity. Areas of altered neuronal activity can therefore be identified as target sites for stimulation. Still further, a target site for stimulation can also include areas identified in the cortex are undergoing or have undergone reorganization.

Additional target sites also include, but are not limited to the cerebellum, which can also be activated in sensory stimulation Thus, other targets can also include any region of the brain associated or in communication with the sensory cortex, which includes any region or structure, as well as any connections to and from the sensory cortex. Association with the sensory cortex includes the functional areas of the sensory cortex for example, but not limited to the primary somatosensory cortex, the secondary somatosensory cortex, the somatosensory association complex, primary visual cortex, secondary and tertiary visual cortices, visual association cortex, primary auditory cortex, auditory association cortex, gustatory cortex, and vestibular cortex, other brain regions that receive somatic inputs, for example, the posterior parietal lobe, as well as any brain region that is stimulated by sensory stimulation, such as the cerebellum. Thus, stimulation of the sensory cortex includes the somatosensory processing cortical regions of the brain and sub-cortical regions or structures, as well as the any brain region in which there are projection connections for example, the basal ganglia, the striatum, the motor cortex, supplementary motor cortex or area, the posterior parietal cortex, the thalamus (e.g., the ventral posterior nucleus of the thalamus), brainstem, periaqueductal grey, dorsal column nuclei, and the spinal cord (e.g., dorsal horn of the spinal cord).

Accordingly, the present invention relates to modulation of neuronal invention finds particular application in the modulation of neuronal function or processing to affect a functional outcome. The modulation of neuronal function is particularly useful with regard to the prevention, treatment, or amelioration of neurological, psychiatric, psychological, conscious state, behavioral, mood, and thought activity (unless otherwise indicated these will be collectively referred to herein as "neurological activity" which includes "psychological activity" or "psychiatric activity"). When referring to a pathological or undesirable condition associated with the activity, reference may be made to a neurological disorder which includes "psychiatric disorder" or "psychological disorder" instead of neurological activity or psychiatric or psychological activity. Although the activity to be modulated usually manifests itself in the form of a disorder such as a attention or cognitive disorders (e.g., Autistic Spectrum Disorders); mood disorder (e.g., major depressive disorder, bipolar disorder, and dysthymic disorder) or an anxiety disorder (e.g., panic disorder, posttraumatic stress disorder, obsessive-compulsive disorder and phobic disorder); neurodegenerative diseases (e.g., multiple sclerosis, Alzheimer's disease, amyotrophic lateral sclerosis (ALS), Parkinson's disease, Huntington's Disease, Guillain-Barre syndrome, myasthenia gravis, and chronic idiopathic demyelinating disease (CID)), movement disorders (e.g., dyskinesia, tremor, dystonia, chorea and ballism, tic syndromes, Tourette's Syndrome, myoclonus, drug-induced movement disorders, Wilson's Disease, Paroxysmal Dyskinesias, Stiff Man Syndrome and Akinetic-Ridgid Syndromes and Parkinsonism), epilepsy, tinnitus, pain, phantom pain, diabetes neuropathy, one skilled in the art appreciates that the invention may also find application in conjunction with enhancing or diminishing any neurological or psychiatric function, not just an abnormality or disorder. Neurological activity that may be modulated can include, but not be limited to, normal functions such as alertness, conscious state, drive, fear, anger, anxiety, repetitive behavior, impulses, urges, obsessions, euphoria, sadness, and the fight or flight response, as well as instability, vertigo, dizziness, fatigue, fotofobia, fonofobia, concentration dysfunction, memory disorders, symptoms of traumatic brain injury (whether physical, emotional, social or chemical), autonomic functions, which includes sympathetic and/or parasympathetic functions (e.g., control of heart rate), somatic functions, and/or enteric functions.

Particular embodiments of the present invention may provide one or more technical advantages. According to the present invention, an electrical stimulation system is used to provide therapeutic electrical stimulation to target tissue in a person's brain to treat a neurological condition. In particular, brain mapping or brain imaging information and/or neurophysiological information (e.g., evoked potentials, induced potentials, EEG, MEG) can be used to identify target tissue in a person's brain having a notable level of activity associated with a neurological condition, such as pain or tinnitus, for example. Such techniques to map the brain include, but are not limited to positron emission tomography (PET), magnetic resonance imaging (MRI), functional MRI (fMRI), electroencephalography (EEG), magnetoencephalography (MEG), x-ray computed tomography (CT), single photon emission computed tomography (SPECT), brain electrical activity mapping (BEAM), transcranial magnetic stimulation (TMS), electrical impedance tomography (EIT), near-infrared spectroscopy (NIRS) and optical imaging.

The brain mapping information may include imaging information obtained by imaging at least a portion of the person's brain using one or more imaging techniques. Instead or in addition, the brain imaging information may include imaging information obtained from imaging of the brains of one or more other patients who experience the same or similar condition as the person. In certain embodiments, an electrode or an electrical stimulation lead having a number of electrodes is implanted inside a person's skull such that one or more of the electrodes are located in communication with the identified target tissue in the brain. The electrodes deliver electrical stimulation pulses to the identified target tissue, which partially or completely alleviates the condition in the person's body, which may significantly increase the person's quality of life. The electrode or electrical stimulation lead may be precisely positioned using a neuronavigation system that includes brain imaging information and mapping data obtained from the imaging of the person's brain or from the imaging of the brains of one or more other patients. In addition, non-invasive transcranial magnetic stimulation (TMS) of the target tissue may be performed before surgically implanting the electrical stimulation lead in order to determine whether the person is a candidate for receiving an implanted electrical stimulation system.

In certain embodiments, the electrical stimulation system may also be able to provide electrical stimulation of the same or different target tissue in the brain to reduce, enhance, or otherwise treat neuroplasticity effects that may be associated with the electrical stimulation of the target tissue for treating the neurological condition. As a result, in certain embodiments, the efficacy period associated with a particular set of stimulation parameters may be extended. This may help prevent the additional time and expense associated with one or more return visits to the treating physician for determining and entering new sets of efficacious parameters. Especially where the treatment is to continue over a relatively long period of time, such as a number of months or years, avoiding this additional time and expense may provide a significant advantage. As another example, in other situations, the further development of neuroplasticity effects already in existence due to injury or disease may be prevented, delayed, or otherwise reduced, or such pre-existing neuroplasticity effects may be reversed in whole or in part. As a result, in certain embodiments, undesirable conditions resulting from such pre-existing neuroplasticity effects may be prevented from progressing further, may be reduced, or may even be eliminated. In certain other embodiments, such as where the person has experienced a stroke, for example, the electrical stimulation system may provide electrical stimulation of the same or different target tissue in the brain to enhance or promote neuroplasticity effects.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE SEVERAL VIEWS OF THE DRAWING

For a more complete understanding of the present invention, reference is now made to the following descriptions taken in conjunction with the accompanying drawing, in which:

FIG. 11A shows a postoperative X-ray demonstrating the position of the lead. FIG. 11B shows postoperative CT comparison to preoperative fMRI (FIG. 11C). Comparing the anatomy of the preoperative fMRI with the postoperative CT scan demonstrates the lead is positioned over the somatosensory cortex. The area of the V1 pain sensation is located more caudally (FIG. 9) and cannot be seen on these images.

DETAILED DESCRIPTION

Figure 1A:
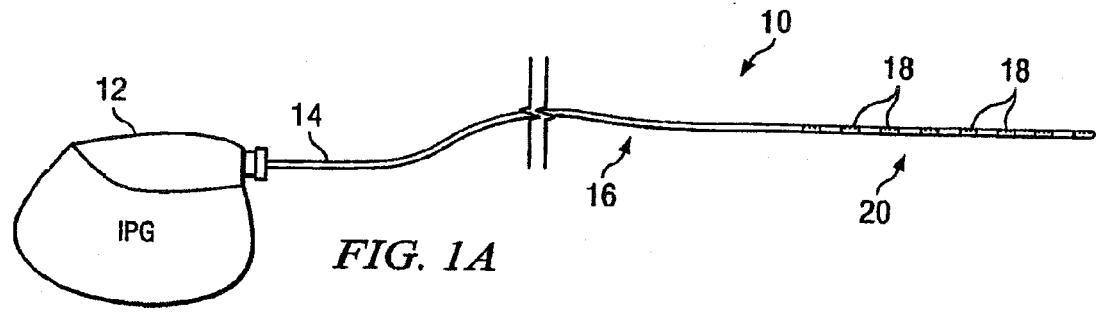
FIGS. 1A-1B illustrate example electrical stimulation systems for electrically stimulating target nerve tissue in the brain identified through imaging of the brain to treat a condition in the body and, in certain embodiments, provide reduced or enhanced neuroplasticity effects in the brain.

It is readily apparent to one skilled in the art that various embodiments and modifications can be made to the invention disclosed in this Application without departing from the scope and spirit of the invention.

I. Definitions

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

As used herein, the term "affective disorders" refers to a group of disorders that are commonly associated with co-morbidity of depression and anxiety symptoms.

As used herein, the term "chronic pain" can generally be characterized as being nociceptive or non-nociceptive including neuropathic pain. Yet further, it can also be characterized as pain that has lasted for a period of time, for example, more than three months. Chronic pain generally also has significant psychological and emotional affects and can limit a person's ability to fully function.

As used herein, the term "acute pain" refers to more a recent onset of pain, pain associated with an injury or trauma or immediate pain triggered by injury. Acute pain can also be referred to as "phasic." Generally, acute pain is associated with a greater intensity of pain and/or an impairment in functionality for the person.

As used herein, the term "sub-acute pain" refers to slow, insidious onset of pain, which can also be characterized as dull and achy. At times, sub-acute pain can not be easily localized, however, it may be possible to localize the pain depending upon the condition. Typically, sub-acute pain creates a discomfort for the person, but does not typically impair functionality for the person.

As used herein, the term "dementia" refers to the loss, of cognitive and intellectual functions without impairment of perception or consciousness. Dementia is typically characterized by disorientation, impaired memory, judgment, and intellect, and a shallow labile affect.

As used herein, the term "deafferentation" refers to a loss of the sensory input from a portion of the body.

As used herein, the term "in communication" refers to the stimulation lead being adjacent, in the general vicinity, in close proximity, or directly next to or directly on the predetermined stimulation site, for example an area of the cortex, or an area associated with the sensory cortex, or any subcortical area or structure that is projections to or from the sensory cortex, or any identified brain region or area determined by mapping the brain of a subject suffering from a neurological condition. Thus, one of skill in the art understands that the lead or electrode is "in communication" with the target tissue or site if the stimulation results in a modulation of neuronal activity resulting in the desired response, such as modulation of the neurological disorder.

The terms "mammal," "mammalian organism," "subject," or "patient" or "person" are used interchangeably herein and include, but are not limited to, humans, dogs, cats, horses and cows. The preferred patients are humans.

As used herein the term "modulate" refers to the ability to regulate positively or negatively neuronal activity. Thus, the term modulate can be used to refer to an increase, decrease, masking, altering, overriding or restoring of neuronal activity.

As used herein, the term "neurology" or "neurological" refers to conditions, disorders, and/or diseases that are associated with the nervous system. The nervous system comprises two components, the central nervous system, which is composed of the brain and the spinal cord, and the peripheral nervous system, which is composed of ganglia and the peripheral nerves that lie outside the brain and the spinal cord. One of skill in the art realizes that the nervous system may be separated anatomically, but functionally they are interconnected and interactive. Yet further, the peripheral nervous system is divided into the autonomic system (parasympathetic and sympathetic), the somatic system and the enteric system. Thus, any condition, disorder and/or disease that effects any component or aspect of the nervous system (either central or peripheral) is referred to as a neurological condition, disorder and/or disease. As used herein, the term "neurological" or "neurology" encompasses the terms "neuropsychiatric" or "neuropsychiatry" and "neuropsychological" or "neuropsychological". Thus, a neurological disease, condition, or disorder includes, but is not limited to cognitive disorders, affective disorders, movement disorders, mental disorders, pain disorders, sleep disorders, etc. For non-inclusive examples, neurological disorders include pain, chronic pain, tinnitus, stroke, hypertension, migraine headaches, depression, and epilepsy.

As used herein, the term "neuropsychiatry" or "neuropsychiatric" refers to conditions, disorders and/or diseases that relate to both organic and psychic disorders of the nervous system.

As used herein, the term "neuropsychological" or "neuropsychologic" refers to conditions, disorders and/or disease that relate to the functioning of the brain and the cognitive processors or behavior.

As used herein, the term "neuronal" or "nervous" refers to a neuron which is a morphologic and functional unit of the brain, spinal column, and peripheral nerves.

As used herein, the term "nociceptive pain" involves direct activation of the nociceptors, such as mechanical, chemical, and thermal receptors, found in various tissues, such as bone, muscle, vessels, viscera, and cutaneous and connective tissue. Nociceptive pain can also be referred to as somatic pain. The afferent somatosensory pathways are thought to be intact in nociceptive pain and examples of such pain include cancer pain from bone or tissue invasion, non-cancer pain secondary to degenerative bone and joint disease or osteoarthritis, and failed back surgery.

As used herein, the term "non-nociceptive pain" occurs in the absence of activation of peripheral nociceptors. Non-nociceptive pain can also be referred to as neuropathic pain, or deafferentation pain. Non-nociceptive pain often results from injury or dysfunction of the central or peripheral nervous system. Such damage may occur anywhere along the neuroaxis and includes thalamic injury or syndromes (also referred to as central pain, supraspinal central pain, or post-stroke pain); stroke; traumatic or iatrogenic trigeminal (trigeminal neuropathic) brain or spinal cord injuries; phantom limb or stump pain; postherpetic neuralgia; anesthesia dolorosa; brachial plexus avulsion; complex regional pain syndrome I and II; postcordotomy dysesthesia; and various peripheral neuropathies, inclusive of pain associated with or related to vascular pathology (vasculitis, angina pectoris, etc.) both peripheral vascular pathology, central or cerebral vascular pathology, and/or cardiac vascular abnormalities.

The term "pain" as used herein refers to an unpleasant sensation or altered sensory perception. For example, the subject experiences discomfort, distress or suffering. Pain of a moderate or high intensity is typically accompanied by anxiety. Thus, one of skill in the art is cognizant that pain may have dual properties, for example sensation and emotion. Examples of pain or altered sensory perception can include, but are not limited to paresthesias, dysesthesias, synesthesia, hyperalgesia, allodynia, phantom perceptions, pressure feeling, as well as motor system activities depending on sensory input (e.g., Parkinsons, myoclonias, dystonias, tremor, stiff man syndrome, dyskinesia, tremor, dystonia, chorea and ballism, tic syndromes, Tourette's Syndrome, myoclonus, drug-induced movement disorders, Wilson's Disease, Paroxysmal Dyskinesias, Stiff Man Syndrome and Akinetic-Ridgid Syndromes and Parkinsonism, etc.). Pain can include chronic pain, acute pain or subacute pain.

As used herein, the term "somatosensory system" refers to the peripheral nervous system division comprising primarily afferent somatic sensory neurons and afferent visceral sensory neurons that receive sensory information from skin and deep tissue, including the 12 cranial and 21 spinal nerves.

As used herein, the term "somatosensory cortex" or "sensory cortex" includes the primary somatosensory cortex, secondary somatosensory cortex and the somatosensory association cortex, as well as the Brodmann areas associated therewith. Still further, the sensory cortex includes all cortical sites having projections to or from the sensory cortex, as well as the subcortical sites having projections to or from the sensory cortex.

As used herein, the term "primary somatosensory cortex" refers to the brain region located in the postcentral gyrus and in the posterior part of the paracentral lobule. The primary somatosensory cortex also includes Brodmann areas 3, 1 and 2.

As used herein, the term "secondary somatosensory cortex" refers to the brain region that lies ventral to the primary somatosensory area along the superior bank of the lateral sulcus.

As used herein, the term "somatosensory association cortex" refers to the brain areas of the superior parietal lobule, and supramarginal gyrus. The somatosensory association cortex also includes Brodmann areas 5, 7, and 40.

As used herein, the term "stimulate" or "stimulation" refers to electrical, chemical, magnetic, heat/cold and/or ultrasonic stimulation that modulates the predetermined sites in the brain.

As used herein, the term "treating" and "treatment" refers to stimulating a peripheral nervous tissue site so that the subject has an improvement in the disease, for example, beneficial or desired clinical results. For purposes of this invention, beneficial or desired clinical results include, but are not limited to, alleviation of symptoms, alleviation of pain, diminishment of extent of disease, stabilized (i.e., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

As used herein, the term "proximate" means on, in, adjacent, or near. Thus, one or more of the electrodes on an electrical stimulation lead are adapted to be positioned on, in, adjacent, or near the identified target tissue in the brain.

As used herein, the term "tissue in the brain" includes any tissue in any associated with the brain, including gray matter and white matter that make up the brain.

II. Electrical Stimulation System

According to the present invention, an electrical stimulation system is used to electrically stimulate target tissue in a person's brain to treat a neurological condition. The target tissue can be in a cortical region of the brain, for example, the somatosensory cortex, which includes the primary, the secondary somatosensory cortex, and the somatosensory association complex. Still further, the somatosensory cortex also includes Brodmann areas 1, 2, 3, 5, and 7. The somatosensory cortex, in certain embodiments, is stimulated either directly or indirectly to treat pain.

Yet further, an another embodiment of the present invention comprises, at least a portion of a person's brain is imaged using one or more imaging techniques to identify target tissue in the brain having a notable level of activity, such as overactivity or underactivity, for example, associated with a condition, such as pain or tinnitus. An electrical stimulation lead having a number of electrodes is implanted inside a person's skull such that one or more of the electrodes are located in communication with the identified target tissue in the brain.

The electrodes deliver electrical stimulation pulses to the identified target brain tissue to adjust the level of activity in the identified target nerve tissue in the brain to treat the neurological condition. For example, if the identified target tissue in the brain is overactive, the one or more electrodes may deliver appropriate electrical stimulation pulses to decrease the activity of the identified target tissue to treat the condition. Similarly, if the identified target tissue in the brain is underactive, the one or more electrodes may deliver appropriate electrical stimulation pulses to increase the activity of the identified target tissue to treat the neurological condition.

The neurological condition may be any condition associated with a notable level of activity, such as overactivity or underactivity for example, in the identified target tissue in the person's brain. Example conditions may include pain in a region of the person's body, tinnitus, depression, and other neurological disorders. In some instances, the notable level of activity in the identified target tissue in the person's brain, and thus the condition in the person's body, is caused by damaged, altered or otherwise abnormally functioning nerve tissue in the person's body correlating to the identified target tissue in the person's brain. For example, with respect to pain, damaged, altered or otherwise abnormally functioning nerve tissue in a region of a person's body that causes pain in that region or another region of the person's body may cause overactivity or underactivity in tissue in the person's brain that correlates to the abnormally functioning nerve tissue. As another example, with respect to tinnitus, damaged, altered or otherwise abnormally functioning nerve tissue in a person's auditory system or brain that causes tinnitus may cause overactivity or underactivity in nerve tissue in the person's brain that correlates to the abnormally functioning nerve tissue.

Figure 1B:
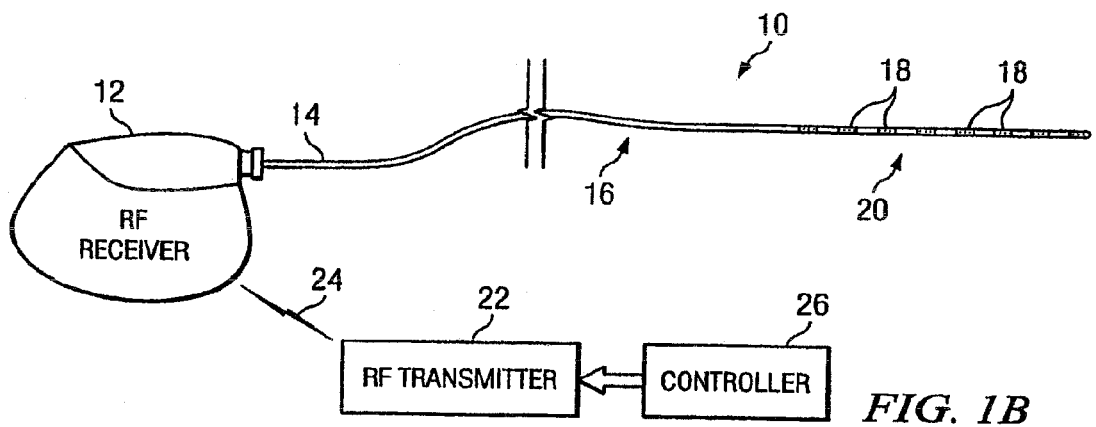

FIGS. 1A-1B illustrate example electrical stimulation systems 10 for electrically stimulating target tissue in the brain identified through imaging of the brain to treat a condition in the body and, in certain embodiments, to provide reduced or enhanced neuroplasticity effects in the brain. Stimulation system 10 generates and applies a stimulus to target tissue in a person's brain, for example, the somatosensory cortex. In certain embodiments, the target tissue is identified through imaging of the person's brain as having a notable level of activity to adjust the level of activity in the identified target tissue to treat a neurological condition.

In general terms, stimulation system 10 includes an implantable electrical stimulation source 12 and an implantable electrical stimulation lead 14 for applying the stimulation signal to the predetermined site or target tissue site. In operation, both of these primary components are implanted in the person's body. In certain embodiments, stimulation source 12 is coupled directly to a connecting portion 16 of electrical stimulation lead 14. In certain other embodiments, stimulation source 12 is not coupled directly to stimulation lead 14 and stimulation source 12 instead communicates with stimulation lead 14 via a wireless link. For example, such a stimulation system 10 are described in the following U.S. Pat. Nos. 6,748,276; 5,938,690, each of which is incorporated by reference in its entirety. In certain other embodiments, stimulation source 12 and electrodes 18 are contained in an "all-in-one" microstimulator or other unit, such as a Bion® microstimulator manufactured by Advanced Bionics Corporation. In any case, stimulation source 12 controls the electrical stimulation pulses transmitted to electrodes 18 (which may be located on a stimulating portion 20 of an electrical stimulation lead 14), implanted in communication with the target tissue, according to appropriate stimulation parameters (e.g., duration, amplitude or intensity, frequency, etc.). A doctor, the patient, or another user of stimulation source 12 may directly or indirectly input or modify stimulation parameters to specify or modify the nature of the electrical stimulation provided.

In one embodiment, as shown in FIG. 1A, stimulation source 12 includes an implantable pulse generator (IPG). An example IPG may be one manufactured by Advanced Neuromodulation Systems, Inc., such as the Genesis® System, part numbers 3604, 3608, 3609, and 3644. In another embodiment, as shown in FIG. 1B, stimulation source 12 includes an implantable wireless receiver. An example wireless receiver may be one manufactured by Advanced Neuromodulation Systems, Inc., such as the Renew® System, part numbers 3408 and 3416. The wireless receiver is capable of receiving wireless signals from a wireless transmitter 22 located external to the person's body. The wireless signals are represented in FIG. 1B by wireless link symbol 24. A doctor, the patient, or another user of stimulation source 12 may use a controller 26 located external to the person's body to provide control signals for operation of stimulation source 12. Controller 26 provides the control signals to wireless transmitter 22, wireless transmitter 22 transmits the control signals and power to the wireless receiver of stimulation source 12, and stimulation source 12 uses the control signals to vary the stimulation parameters of electrical stimulation pulses transmitted through electrical stimulation lead 14 to the stimulation site.

An example wireless transmitter 122 may be one manufactured by Advanced Neuromodulation Systems, Inc., such as the Renew® System, part numbers 3508 and 3516.

FIGS. 2A-2I illustrate example electrical stimulation leads 14 that may be used to provide electrical stimulation to a target brain tissue site. As described above, each of the one or more leads 14 incorporated in stimulation system 10 includes one or more electrodes 18 adapted to be positioned near the target tissue site and used to deliver electrical stimulation energy to the target tissue site in response to electrical signals received from stimulation source 12. A percutaneous lead 14, such as example leads shown in FIGS. 4A-4D, includes one or more circumferential electrodes 18 spaced apart from one another along the length of lead 14. An example of an eight-electrode percutaneous lead is an OCTRODE® lead manufactured by Advanced Neuromodulation Systems, Inc. A stimulation system such as is described in U.S. Pat. No. 6,748,276 is also contemplated. Circumferential electrodes 18 emit electrical stimulation energy generally radially in all directions.

A laminotomy, paddle, or surgical stimulation lead 14, such as example stimulation leads 14 described in FIGS. 2E-I, includes one or more directional stimulation electrodes 18 spaced apart from one another along one surface of stimulation lead 14. An example of an eight-electrode, two column laminotomy lead is a LAMITRODE® and C-series LAMITRODE® 44 leads manufactured by Advanced Neuromodulation Systems, Inc. Directional stimulation electrodes 18 emit electrical stimulation energy in a direction generally perpendicular to the surface of stimulation lead 14 on which they are located.

Although various types of stimulation leads 14 are shown as examples, the present invention contemplates stimulation system 10 including any suitable type of stimulation lead 14 in any suitable number. In addition, stimulation leads 14 may be used alone or in combination. In addition, the leads may be used alone or in combination. For example, unilateral stimulation of nerve tissue in the brain is typically accomplished using a single lead 14 implanted in one side of the brain, while bilateral stimulation of the brain is typically accomplished using two leads 14 implanted in opposite sides of the brain.

Whether using percutaneous leads, laminotomy leads, or some combination of both, the leads are coupled to one or more conventional neurostimulation devices, or signal generators. The devices can be totally implanted systems and/or radio frequency (RF) systems. An example of an RF system is a MNT/MNR-916CC system manufactured by Advanced Neuromodulation Systems, Inc.

The preferred neurostimulation systems should allow each electrode of each lead to be defined as a positive, a negative, or a neutral polarity. For each electrode combination (i.e., the defined polarity of at least two electrodes having at least one cathode and at least one anode), an electrical signal can have at least a definable amplitude (i.e., voltage), pulse width, and frequency, where these variables may be independently adjusted to finely select the sensory transmitting nerve tissue required to inhibit transmission of neuronal signals. Generally, amplitudes, pulse widths, and frequencies are determinable by the capabilities of the neurostimulation systems.

Voltage or intensity that can be used may include a range from about 1 millivolt to about 1 volt or more, e.g., 0.1 volt to about 50 volts, e.g., from about 0.2 volt to about 20 volts and the frequency may range from about 1 Hz to about 2500 Hz, e.g., about 1 Hz to about 1000 Hz, e.g., from about 2 Hz to about 100 Hz in certain embodiments. The pulse width may range from about 1 microsecond to about 2000 microseconds or more, e.g., from about 10 microseconds to about 2000 microseconds, e.g., from about 15 microseconds to about 1000 microseconds, e.g., from about 25 microseconds to about 1000 microseconds The electrical output may be applied for at least about 1 millisecond or more, e.g., about 1 second, e.g., about several seconds, where in certain embodiments the stimulation may be applied for as long as about 1 minute or more, e.g., about several minutes or more, e.g., about 30 minutes or more may be used in certain embodiments.

It is envisaged that the patient will require intermittent assessment with regard to patterns of stimulation. Different electrodes on the lead can be selected by suitable computer programming, such as that described in U.S. Pat. No. 5,938,690, which is incorporated by reference here in full. Utilizing such a program allows an optimal stimulation pattern to be obtained at minimal voltages. This ensures a longer battery life for the implanted systems.

In certain embodiments, the electrical stimulation system of the present invention includes a system that is capable of being programmed with three or more stimulation settings to generate a corresponding number of electrical stimulation pulses. These and other objects of the system are obtained by providing a microcomputer controlled system. To control the stimulation setting and associated amplitude broadcast to the receiver, the transmitter includes a programmable setting time generator which is controlled by the microcomputer. The setting time generator generates a treatment interval which is sent to a programmable setting counter. The treatment interval is the interval that a particular stimulation setting is broadcast before the transmitter switches to the next stimulation setting. In the "simultaneous" operations mode, the treatment modality is set such that the patient cannot discern the switching between stimulation setting intervals, or pulses, and feels only the cumulative effect of all settings. The setting counter uses the treatment interval to control the select lines of the setting and amplitude multiplexers. The counter allows the setting counter to cycle through the desired stimulation settings substantially sequentially and ensures that all elected settings are broadcast. The system further includes a clock to provide a signal at a continuous frequency. Similar systems are further described in U.S. Pat. No. 6,609,031, U.S. Provisional Application No. 60/561,437, entitled "Pulse Generator Circuit Universal Custom Output Driver" filed Apr. 12, 2004, U.S. Provisional Application No. 60/648,556, entitled "Efficient Fractional Voltage Converter" filed Jan. 31, 2005, and U.S. Provisional Application No. 60/568,384, entitled "Multi-Programmable Trial Stimulator" filed May 5, 2004, each of which is incorporated herein by reference in its entirety.

III. Implantation of System

One technique that offers the ability to affect neuronal function is the delivery of electrical stimulation for neuromodulation directly to target tissues via an implanted system having an electrode. The electrode can also be comprised within a stimulation lead. The electrode is coupled to system to stimulate the target site.

Techniques for implanting electrodes or stimulation leads such as stimulation lead 14 are known to those skilled in the art. In certain embodiments, for example, patients who are to have an electrical stimulation lead or electrode implanted into the brain, generally, first have a stereotactic head frame, such as the Leksell, CRW, or Compass, mounted to the patient's skull by fixed screws. However, frameless techniques may also be used. Subsequent to the mounting of the frame, the patient typically undergoes a series of magnetic resonance imaging sessions, during which a series of two dimensional slice images of the patient's brain are built up into a quasi-three dimensional map in virtual space. This map is then correlated to the three dimensional stereotactic frame of reference in the real surgical field. In order to align these two coordinate frames, both the instruments and the patient must be situated in correspondence to the virtual map. The current way to do this is to rigidly mount the head frame to the surgical table. Subsequently, a series of reference points are established to relative aspects of the frame and patient's skull, so that either a person or a computer software system can adjust and calculate the correlation between the real world of the patient's head and the virtual space model of the patient MRI scans. The surgeon is able to target any region within the stereotactic space of the brain with precision (e.g., within 1 mm). Initial anatomical target localization is achieved either directly using the MRI images or functional imaging (PET or SPECTscan, fMRI, MSI), or indirectly using interactive anatomical atlas programs that map the atlas image onto the stereotactic image of the brain. As is described in greater detail elsewhere in this application, the anatomical targets or predetermined site or target site may be stimulated directly or affected through stimulation in another region of the brain.

Figure 3:
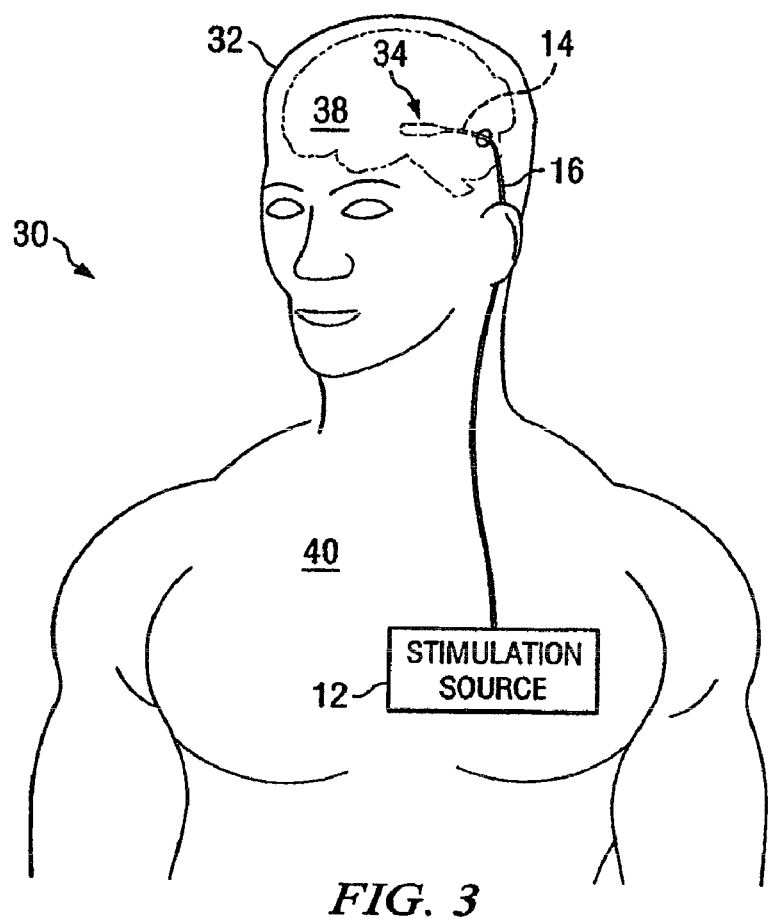
FIG. 3 illustrates example placement of the electrical stimulation system shown in FIGS. 1A-1B within a person's body.

FIG. 3 illustrates example placement of the electrical stimulation system 10 shown in FIGS. 1A-1B within a person's body 30. Electrical stimulation lead 14 is implanted under the person's skull 32 proximate or in communicate with a particular region of the person's brain. In certain embodiments, electrical stimulation lead 14 is positioned within the extradural region adjacent the brain such that one or more electrodes 18 are located proximate target nerve tissue 34 within one or more regions 38 of the brain, for example, the frontal lobe, the occipital lobe, the parietal lobe, the temporal lobe, the cerebellum, or the brain stem. More particularly, the target tissue 34 in the brain may be located in one or more of the somatosensory cortex, more particularly, the primary somatosensory cortex or the secondary somatosensory cortex or the somatosensory association complex, or associated with the somatosensory cortex.

Additional target sites also include, but are not limited to the cerebellum, which can also be activated in sensory stimulation. Thus, other targets can also include any cortical region of the brain associated or in communication with the sensory cortex, as well as any subcortical region of the brain in association or communication with the sensory cortex. Regions of the brain that are in association with the sensory cortex includes the functional areas of the sensory cortex for example, but not limited to the primary somatosensory cortex, the secondary somatosensory cortex, the somatosensory association complex, primary visual cortex, secondary and tertiary visual cortices, visual association cortex, primary auditory cortex, auditory association cortex, gustatory cortex, and vestibular cortex, other brain regions that receive somatic inputs, for example, the posterior parietal lobe, as well as any brain region that is stimulated by sensory stimulation, such as the cerebellum. Thus, stimulation of the sensory cortex includes the somatosensory processing cortical regions of the brain and sub-cortical regions or structures, as well as the any brain region in which there are projection connections for example, the basal ganglia, the striatum, the motor cortex, the posterior parietal cortex, the thalamus (e.g., the ventral posterior nucleus of the thalamus), brainstem, dorsal column nuclei, and the spinal cord (e.g., dorsal horn of the spinal cord).

In certain embodiments, the target sites may include brain areas that are known to be involved in pain perception for example the lateral thalamus, primary and second somatosensory regions, the insular cortex, the posterior parietal cortex, the prefrontal cortex, periaqueductal grey, basal ganglia, supplementary motor cortex or area, and cerebellum. More particularly, the target sites may include the areas or regions implicated in pain inhibition, for example, but not limited to periaqueductal grey, basal ganglia, supplementary motor cortex or area, and cerebellum.

Still further other target sites include, but are not limited to the putamen, the thalamus, the insula, the anterior cingulate cortex, the supplementary motor area, the frontal operculum, the auditory cortex, such as the primary auditory cortex, AI, also known as the transverse temporal gyri of Heschl (Brodmann's areas 41 and 42), the secondary auditory cortex, AII (Brodmann's areas 22 and 52), the remote projection region, the ventral medial geniculate, which projects almost entirely to AI, the surrounding auditory areas, which receive projections from the rest of the geniculate body, and the medial geniculate body, which is the major auditory nucleus of the thalamus. Other target areas can include those identified by the methodology discussed below.

In certain embodiments, electrical stimulation lead 14 is located at least partially within or below the dura mater proximate target tissue 34. For example, electrical stimulation lead 14 may be inserted into the cortex or deeper layers of the brain.

Stimulation source 12 is implanted within a subcutaneous pocket within the person's torso 40 (such as in or near the chest area or buttocks), and connecting portion 16 is tunneled, at least in part, subcutaneously underneath the person's skin to connect stimulation source 12 with the electrical stimulation lead 14. However, stimulation source 12 may be located at any suitable location within the person's body 30 according to particular needs.

Figure 4:
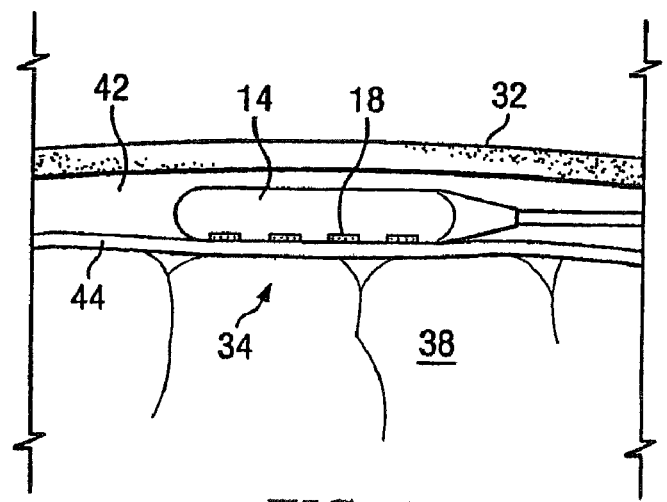
FIG. 4 is a cross-section of a portion of the person's head shown in FIG. 3, illustrating an example location of the electrical stimulation lead.

FIG. 4 is a cross-section of a portion of the person' head shown in FIG. 3, illustrating an example location of electrical stimulation lead 14. In certain embodiments, as discussed above, electrical stimulation lead 14 is located in the extradural region 42 outside the dura mater 44 and proximate target nerve tissue 34 within one or more regions 38 of the brain. In other embodiments, the electrical stimulation lead 14 is located in an intradural region inside the dura mater and proximate target tissue within one or more regions of the brain.

In certain embodiments of the present invention, the target site or brain region to be stimulated is determined using techniques that measure altered neuronal activity in the brain. For example, the brain of an afflicted person is imaged or mapped using standard techniques to determine altered neuronal activity includes overactive or underactive activity. The brain imaging information indicates whether the identified target tissue site or brain region is overactive or underactive and the degree or intensity of such overactivity or underactivity. Techniques used may include, for example, positron emission tomography (PET), magnetic resonance imaging (MRI), functional MRI (fMRI), electroencephalography (EEG), magnetoencephalography (MEG), x-ray computed tomography (CT), single photon emission computed tomography (SPECT), brain electrical activity mapping (BEAM), transcranial magnetic stimulation (TMS), electrical impedance tomography (EIT), near-infrared spectroscopy (NIRS), and optical imaging.

Figure 5:
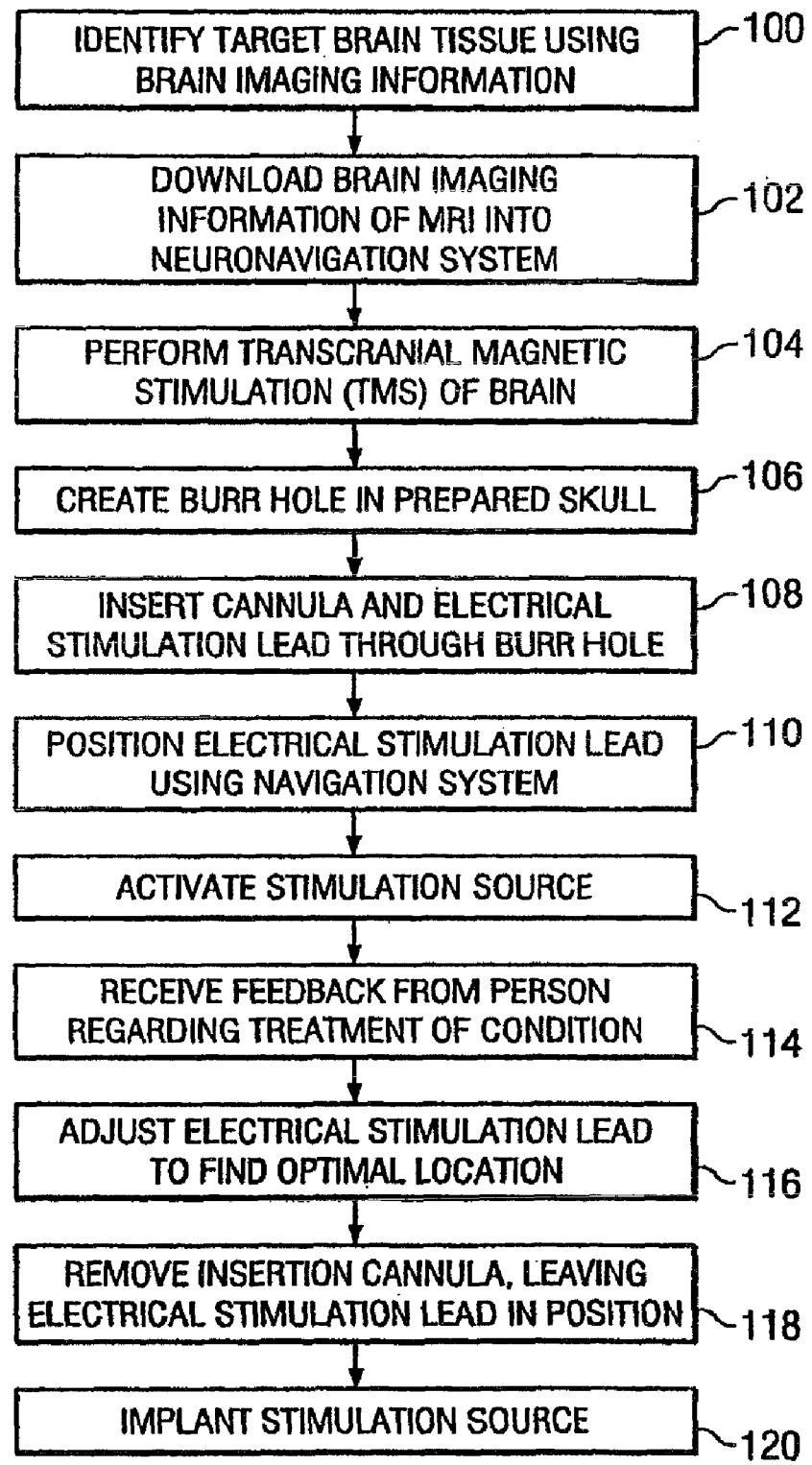
FIG. 5 illustrates an example method for determining an optimal location and implanting the stimulation system of FIGS. 1A-1B into a person in order to electrically stimulate target nerve tissue in the brain identified through imaging of the brain to treat a condition in the body.

FIG. 5 illustrates an example method for determining an optimal location and implanting or placing a stimulation system described above into a person in order to electrically stimulate a target site.

In certain embodiments, the target brain tissue to be stimulated is identified using standard brain mapping techniques, such as imaging techniques, as well as other neurophysiological techniques such as EEG, MEG, nerve condition studies. Techniques used to map the brain may include, for example, positron emission tomography (PET), magnetic resonance imaging (MRI), functional MRI (fMRI), electroencephalography (EEG), magnetoencephalography (MEG), x-ray computed tomography (CT), single photon emission computed tomography (SPECT), brain electrical activity mapping (BEAM), transcranial magnetic stimulation (TMS), electrical impedance tomography (EIT), near-infrared spectroscopy (NIRS), nerve condition studies, and optical imaging. For additional description of identifying targets in a person's brain, see U.S. application Ser. No. 10/993,888, which is incorporated herein by reference in its entirety.

At step 100, at least a portion of the person's brain may be imaged and/or mapped to obtain neuronal information that identifies a target site in the brain having a notable level of activity, such as overactivity or underactivity for example, which could be associated with a neurological condition. The utilization of techniques to map the brain enables one of skill in the art to determine the area of the brain in which there is an altered neuronal activity. Such altered neuronal activity can be associated with reorganization of neuronal cells, such as cortical reorganization. The information obtained from these maps provide one of skill in the art with the knowledge of determining the brain region that has an altered activity that is associated with a neurological condition or can be correlated with the neurological condition. In certain embodiments, it is necessary to perform these mapping studies to identify the target site so that the appropriate brain region is stimulated to result in treatment of the neurological condition without such mapping it may be difficult to determine the brain region to stimulate to achieve the optimum benefit from the electrical stimulation.

Those in the art will understand that this technique may be used as confirmation or investigation of the notable level of activity of the target tissue. Additionally, those in the art will understand that the location of the target tissue in the person's brain may be determined using information from brain imaging studies performed on other patients, and thus the imaging of the person's brain at step 100 may not be performed. Such brain imaging studies may include imaging information obtained using one or more of the imaging techniques listed above to image the brains of patients suffering from various types of neurological conditions. The location of tissue in the brain correlating to various conditions may be identified using statistical analysis of such mapping information (imaging and/or neurophysiological studies). Thus, at step 100, target tissue in the person's brain correlated to the neurological condition may be identified according to the results of such brain imaging studies.

At step 102, the brain imaging information obtained at step 100 (whether from imaging the person's brain or from imaging studies of other patients suffering from the same or similar condition as the person) is downloaded into a neuronavigation system.

At step 104, TMS of the an area of the person's brain, such as an area proximate the target brain tissue identified at step 100 for example, may be performed to determine whether the person is a candidate for receiving an implanted electrical stimulation system 10. The TMS process, which is a non-invasive technique of activating or deactivating focal areas of the brain, may be guided by the navigation system that includes the brain imaging information obtained at step 100. If the TMS process is successful in treating the condition in the person's body, the person may be considered for receiving an implanted electrical stimulation system 10. Those of skill in the art realize that step 104 is not essential. In fact, in certain embodiments of the present invention, the method skips step 104. Thus, the sequence is step 102 directly to step 106.

Electrical stimulation system 10 is implanted or placed inside the person at steps 106 through 118. At step 106, the skull 32 is first prepared by exposing the skull 32 and creating a burr hole in the skull 32. A burr hole cover may be seated within the burr hole and fixed to the scalp or skull 32. Stereotactic equipment suitable to aid in placement of an electrical stimulation lead 14 in the brain may be positioned around the head. An insertion cannula for electrical stimulation lead 14 may be inserted through the burr hole into the brain at step 108, but a cannula is not typically used where lead 14 is a laminotomy or paddle lead 14. A cannula and electrical stimulation lead 14 may be inserted together or lead 14 may be inserted through the cannula after the cannula has been inserted. Guided by the navigation system that includes the brain imaging information obtained at step 100, electrical stimulation lead 14 is precisely positioned proximate the brain at step 110 such that one or more electrodes 18 are located proximate the target nerve tissue in the brain identified at step 100. In certain embodiments, electrical stimulation lead 14 is positioned extradurally, such as shown in FIG. 4.

At step 112, stimulation source 12 is activated, which generates and sends electrical stimulation pulses via electrical stimulation lead 14 to the target nerve tissue proximate one or more electrodes 18 on stimulation lead 14. The electrical stimulation pulses delivered to the tissue by electrodes 18 may adjust the activity of the target tissue In an appropriate manner to treat the neurological condition. For example, if the brain imaging information obtained at step 100 indicates that the identified target tissue is overactive, stimulation source 12 may generate, and the one or more electrodes 18 may deliver, appropriate electrical stimulation pulses to decrease the activity of the target tissue proximate the one or more electrodes 18 to treat the neurological condition. Similarly, if the brain imaging information obtained at step 100 indicates that the identified target nerve tissue is underactive, stimulation source 12 may generate, and the one or more electrodes 18 may deliver, appropriate electrical stimulation pulses to increase the activity of the target nerve tissue proximate the one or more electrodes 18 to treat the neurological condition.

At step 114, the person indicates whether the condition in the person's body is adequately alleviated by electrical stimulation system 10. If the condition is not adequately alleviated, electrical stimulation lead 14 may be moved incrementally at step 116 until the person indicates that the condition is adequately alleviated. Once electrical stimulation lead 14 has been positioned in the brain, lead 14 is uncoupled from any stereotactic equipment if present, and the cannula and stereotactic equipment if used are removed. Where stereotactic equipment is used, the cannula may be removed before, during, or after removal of the stereotactic equipment. Connecting portion 16 of electrical stimulation lead 14 is laid substantially flat along the skull. Where appropriate, any burr hole cover seated in the burr hole may be used to secure electrical stimulation lead 14 in position and possibly to help prevent leakage from the burr hole and entry of contaminants into the burr hole. Example burr hole covers that may be appropriate in certain embodiments are illustrated and described in co-pending U.S. Application Nos. 60/528,604 and 60/528,689, both filed Dec. 11, 2003 and entitled "Electrical Stimulation System and Associated Apparatus for Securing an Electrical Stimulation Lead in Position in a Person's Brain", both of which are incorporated herein in their entirety.

Once electrical stimulation lead 14 has been inserted and secured, stimulation source 12 is implanted at step 120. The implant site is typically a subcutaneous pocket formed to receive and house stimulation source 12. The implant site is usually positioned a distance away from the insertion site, such as near the chest area or buttocks or another place in the torso 40. Connecting portion 16 of lead 14 extends from the lead insertion site to the implant site at which stimulation source 12 is implanted. A doctor, the patient, or another user of stimulation source 12 may directly or indirectly input stimulation parameters for controlling the nature of the electrical stimulation provided. Still further, the stimulation parameters can be adjusted accordingly to maintain or achieve the optimum benefit. Such adjustments may require providing neuroplasticity signals or altered signals, increase the signals or enhance the signals, etc. See the below discussion of neuroplasticity, which is incorporated herein. Still further, adjustments can be made by increasing the amount of signals, for example, stimulating more than one location in the brain as described in U.S. Provisional Application No. 60/645,405 entitled "Electrical Stimulation System and Method for Stimulating Multiple Locations of Target Nerve Tissue in the Brain to Treat Multiple Conditions in the Body" filed Jan. 19, 2005, and U.S. Pat. No. 6,609,031 each of which is incorporated herein by reference in its entirety.

Although example steps are illustrated and described, the present invention contemplates two or more steps taking place substantially simultaneously or in a different order. In addition, the present invention contemplates using methods with additional steps, fewer steps, or different steps, so long as the steps remain appropriate for imaging the brain of a person suffering from a condition—or using brain imaging studies regarding patients suffering from the same or similar condition as the person—to identify target nerve tissue having a notable level of activity and implanting an example stimulation system 10 into a person for electrical stimulation of the person's brain to adjust the level of activity in identified target tissue in the person's brain to treat the person's condition.

IV. Methods to Treat Neurological Disorders

The present invention utilizes a stimulation system to alter neuronal activity in the brain. More particularly, the stimulation system can be used to stimulate the brain and cause/allow the brain to act in the best interest of the host through use of the brain's natural mechanisms.

The present disclosure describes apparatuses and systems for applying electrical stimulation to cortical and other sites on a patient. Stimulation systems and methods described herein may be used to treat a variety of neurological conditions. Depending on the nature of a particular condition, neural stimulation applied or delivered in accordance with various embodiments of such systems and/or methods may facilitate or effectuate reorganization of interconnections or synapses between neurons to (a) provide at least some degree of recovery of a lost function; and/or (b) develop one or more compensatory mechanisms to at least partially overcome a functional deficit. Such reorganization of neural interconnections may be achieved, at least in part, by a change in the strength of synaptic connections through a process that corresponds to a mechanism commonly known as Long-Term Potentiation (LTP). Electrical stimulation applied to one or more target neural populations either alone or in conjunction with behavioral activities and/or adjunctive or synergistic therapies may facilitate or effectuate neural plasticity and the reorganization of synaptic interconnections between neurons.

Accordingly, the present invention relates to modulation of neuronal activity to affect neurological, neuropsychological or neuropsychiatric activity. The present invention finds particular application in the modulation of neuronal function or processing to affect a functional outcome. The modulation of neuronal function is particularly useful with regard to the prevention, treatment, or amelioration of neurological, psychiatric, psychological, conscious state, behavioral, mood, and thought activity (unless otherwise indicated these will be collectively referred to herein as "neurological activity" which includes "psychological activity" or "psychiatric activity"). When referring to a pathological or undesirable condition associated with the activity, reference may be made to a neurological disorder which includes "psychiatric disorder" or "psychological disorder" instead of neurological activity or psychiatric or psychological activity. Although the activity to be modulated usually manifests itself in the form of a disorder such as a attention or cognitive disorders (e.g., Autistic Spectrum Disorders); mood disorder (e.g., major depressive disorder, bipolar disorder, and dysthymic disorder) or an anxiety disorder (e.g., panic disorder, posttraumatic stress disorder, obsessive-compulsive disorder and phobic disorder); neurodegeneratove diseases (e.g., multiple sclerosis, Alzheimer's disease, amyotrophic lateral sclerosis (ALS), Parkinson's disease, Huntington's Disease, Guillain-Barre syndrome, myasthenia gravis, and chronic idiopathic demyelinating disease (CID)), movement disorders (e.g., dyskinesia, tremor, dystonia, chorea and ballism, tic syndromes, Tourette's Syndrome, myoclonus, drug-induced movement disorders, Wilson's Disease, Paroxysmal Dyskinesias, Stiff Man Syndrome and Akinetic-Ridgid Syndromes and Parkinsonism), epilepsy, tinnitus, pain, phantom pain, diabetes neuropathy, one skilled in the art appreciates that the invention may also find application in conjunction with enhancing or diminishing any neurological or psychiatric function, not just an abnormality or disorder. Neurological activity that may be modulated can include, but not be limited to, normal functions such as alertness, conscious state, drive, fear, anger, anxiety, repetitive behavior, impulses, urges, obsessions, euphoria, sadness, and the fight or flight response, as well as instability, vertigo, dizziness, fatigue, fotofobia, fonofobia, concentration dysfunction, memory disorders, symptoms of traumatic brain injury (whether physical, emotional, social or chemical), autonomic functions, which includes sympathetic and/or parasympathetic functions (e.g., control of heart rate), somatic functions, and/or enteric functions.

In certain embodiments, neurological disorders or conditions that can be treated using the present invention include, for example, but are not limited to cardiovascular diseases, e.g., atherosclerosis, coronary artery disease, hypertension, hyperlipidemia, cardiomyopathy, volume retention; neuroinflammatory diseases, e.g., viral meningitis, viral encephalitis, fungal meningitis, fungal encephalitis, multiple sclerosis, charcot joint; myasthenia gravis; orthopedic diseases, e.g., osteoarthritis, inflammatory arthritis, reflex sympathetic dystrophy, Paget's disease, osteoporosis; lymphoproliferative diseases, e.g., lymphoma, lymphoproliferative disease, Hodgkin's disease; autoimmune diseases, e.g., Graves disease, hashimoto's, takayasu's disease, kawasaki's diseases, arthritis, scleroderma, CREST syndrome, allergies, dermatitis, Henoch-schlonlein purpura, goodpasture syndrome, autoimmune thyroiditis, myasthenia gravis, Reiter's disease, lupus, rheumatoid arthritis; inflammatory and infectious diseases, e.g., sepsis, viral and fungal infections, wound healing, tuberculosis, infection, human immunodeficiency virus; pulmonary diseases, e.g., tachypnea, fibrotic diseases such as cystic fibrosis, interstitial lung disease, desquamative interstitial pneumonitis, non-specific interstitial pneumonitis, lymphocytic interstitial pneumonitis, usual interstitial pneumonitis, idiopathic pulmonary fibrosis; transplant related side effects such as rejection, transplant-related tachycardia, renal failure, typhlitis; transplant related bowel dysmotility, transplant-related hyperreninemia; sleep disorders, e.g., insomnia, obstructive sleep apnea, central sleep apnea; gastrointestinal disorders, e.g., hepatitis, xerostomia, bowel dysmotility, peptic ulcer disease, constipation, post-operative bowel dysmotility; inflammatory bowel disease; endocrine disorders, e.g., hypothyroidism, hyperglycemia, diabetes, obesity, syndrome X; cardiac rhythm disorders, e.g., sick sinus syndrome, bradycardia, tachycardia, QT interval prolongation arrhythmias, atrial arrhythmias, ventricular arrhythmias; genitourinary disorders, e.g., bladder dysfunction, renal failure, hyperreninemia, hepatorenal syndrome, renal tubular acidosis, erectile dysfunction; cancer; fibrosis; skin disorders, e.g., wrinkles, cutaneous vasculitis, psoriasis; aging associated diseases and conditions, e.g., shy dragers, multi-system atrophy, osteoporosis, age related inflammation conditions, degenerative disorders; autonomic dysregulation diseases; e.g., headaches, concussions, post-concussive syndrome, coronary syndromes, coronary vasospasm; neurocardiogenic syncope; neurologic diseases such as epilepsy, seizures, stress, bipolar disorder, migraines and chronic headaches; conditions related to pregnancy such as amniotic fluid embolism, pregnancy-related arrhythmias, fetal stress, fetal hypoxia, eclampsia, preeclampsia; conditions that cause hypoxia, hypercarbia, hypercapnia, acidosis, acidemia, such as chronic obstructive lung disease, emphysema, cardiogenic pulmonary edema, non-cardiogenic pulmonary edema, neurogenic edema, pleural effusion, adult respiratory distress syndrome, pulmonary-renal syndromes, interstitial lung diseases, pulmonary fibrosis, and any other chronic lung disease; sudden death syndromes, e.g., sudden infant death syndrome, sudden adult death syndrome; vascular disorders, e.g., acute pulmonary embolism, chronic pulmonary embolism, deep venous thrombosis, venous thrombosis, arterial thrombosis, coagulopathy, aortic dissection, aortic aneurysm, arterial aneurysm, myocardial infarction, coronary vasospasm, cerebral vasospasm, mesenteric ischemia, arterial vasospasm, malignant hypertension; primary and secondary pulmonary hypertension, reperfusion syndrome, ischemia, cerebral vascular accident, cerebral vascular accident and transient ischemic attacks; pediatric diseases such as respiratory distress syndrome; bronchopulmonary dysplasia; Hirschprung disease; congenital megacolon, aganglionosis; ocular diseases such as glaucoma; and the like.

The present invention finds particular utility in its application to human neurological disorders, for example psychological or psychiatric activity/disorder and/or physiological disorders and/or other neurological conditions. One skilled in the art appreciates that the present invention is applicable to other animals which exhibit behavior that is modulated by the neuronal tissue. This may include, for example, primates, canines, felines, horses, elephants, dolphins, etc. Utilizing the various embodiments of the present invention, one skilled in the art may be able to modulate neuronal functional outcome to achieve a desirable result.

One technique that offers the ability to affect neuronal function is the delivery of electrical and/or ultrasonic and/or magnetic stimulation for neuromodulation directly to target tissues or predetermined tissue sites via an implanted device having a probe. The probe can be stimulation lead or electrode assembly. The electrode assembly may be one electrode, multiple electrodes, or an array of electrodes in or around the target area. The proximal end of the probe is coupled to a system to operate the device to stimulate the target site. Thus, the probe is coupled to an electrical signal source, which, in turn, is operated to stimulate the target tissue or predetermined site.

Treatment regimens may vary as well, and often depend on the health and age of the patient. Obviously, certain types of disease will require more aggressive treatment, while at the same time, certain patients cannot tolerate more taxing regimens. The clinician will be best suited to make such decisions based on the known subject's history.

The therapeutic system or of the present invention is surgically implanted in the subject's body as described herein. One of skill in the art is cognizant that a variety of electrodes or electrical stimulation leads may be utilized in the present invention. It is desirable to use an electrode or lead that contacts or conforms to the target site for optimal delivery of electrical stimulation. One such example, is a single multi contact electrode with eight contacts separated by 21/2 mm each contract would have a span of approximately 2 mm. Another example is an electrode with two 1 cm contacts with a 2 mm intervening gap. Yet further, another example of an electrode that can be used in the present invention is a 2 or 3 branched electrode to cover the target site. Each one of these three pronged electrodes have four contacts 1-2 mm contacts with a center to center separation of 2 of 2.5 mm and a span of 1.5 mm.

According to one embodiment of the present invention, the target site is stimulated using stimulation parameters such as, pulse width of about 1 to about 500 microseconds, more preferable, about 1 to about 90 microseconds; frequency of about 1 to about 300 Hz, more preferably, about 100 to about 185 Hz; and voltage of about 0.1 to about 10 volts, more preferably about 1 to about 10 volts. It is known in the art that the range for the stimulation parameters may be greater or smaller depending on the particular patient needs and can be determined by the physician. Other parameters that can be considered may include the type of stimulation for example, but not limited to acute stimulation, subacute stimulation, and/or chronic stimulation.

Using the stimulation system of the present invention, the predetermined site or target area is stimulated in an effective amount or effective treatment regimen to decrease, reduce, modulate or abrogate the neurological disorder. Thus, a subject is administered a therapeutically effective stimulation so that the subject has an improvement in the parameters relating to the neurological disorder or condition including subjective measures such as, for example, neurological examinations and neuropsychological tests (e.g. Minnesota Multiphasic Personality Inventory, Beck Depression Inventory, Mini-Mental Status Examination (MMSE), Hamilton Rating Scale for Depression, Wisconsin Card Sorting Test (WCST), Tower of London, Stroop task, MADRAS, CGI, N-BAC, or Yale-Brown Obsessive Compulsive score (Y-BOCS)), motor examination, and cranial nerve examination, and objective measures including use of additional psychiatric medications, such as anti-depressants, or other alterations in cerebral blood flow or metabolism and/or neurochemistry.

Patient outcomes may also be tested by health-related quality of life (HRQL) measures: Patient outcome measures that extend beyond traditional measures of mortality and morbidity, to include such dimensions as physiology, function, social activity, cognition, emotion, sleep and rest, energy and vitality, health perception, and general life satisfaction. (Some of these are also known as health status, functional status, or quality of life measures.)

Functional imaging may also be used to measure the effectiveness of the treatment. This includes electrical methods such as electroencephalography (EEG), magnetoencephalography (MEG), single photon emission computed tomography (SPECT), as well as metabolic and blood flow studies such as functional magnetic resonance imaging (fMRI), and positron emission tomography (PET) which can be utilized to localize brain function and dysfunction. Also, electrophysiological examinations, such as electromyography (EMG) and nerve conduction studies (NCS), can also be utilized to assess the effectiveness of the treatment.

Clinical observations may indicate that the efficacy of treatment may be correlated to the amplitude or intensity. For example, stimulation of the somatosensory cortex may include stimulation parameters that are sub-threshold. In the treatment of pain, the intensity or amplitude of the electrical stimulation of the somatosensory cortex is sub-threshold as to be beneficial to alleviate pain and not exacerbate the pain condition.

In certain embodiments, it may be necessary to monitor the stimulation signals or parameters in the instance that adjustments need to be made to obtain the optimum benefit of the stimulation system. Such monitoring may be performed by the subject or a clinician. Monitoring may include observing any changes in symptoms or any other clinical observations, as well as performing neurophysiological studies, neurological examinations, psychological examinations, functional imaging studies, etc. Based upon the information obtained from this type of monitoring, the stimulation parameters or signals may be adjusted if necessary.

Thus, stimulation signals or the series of electrical or magnetic pulses used can affect neurons within a target neural population. Stimulation signals may be defined or described in accordance with stimulation signal parameters that include pulse amplitude, pulse frequency, duty cycle, stimulation signal duration, and/or other parameters. Electrical or magnetic stimulation signals applied to a population of neurons can depolarize neurons within the population toward their threshold potentials. Depending upon stimulation signal parameters, this depolarization can cause neurons to generate or fire action potentials.

Neural stimulation that elicits or induces action potentials in a functionally significant proportion of the neural population to which the stimulation is applied is referred to as supra-threshold stimulation; neural stimulation that fails to elicit action potentials in a functionally significant proportion of the neural population is defined as sub-threshold stimulation. In general, supra-threshold stimulation of a neural population triggers or activates one or more functions associated with the neural population, but sub-threshold stimulation by itself does not trigger or activate such functions. Supra-threshold neural stimulation can induce various types of measurable or monitorable responses in a patient. For example, supra-threshold stimulation applied to a patient's motor cortex can induce muscle fiber contractions in an associated part of the body to produce an intended type of therapeutic, rehabilitative, or restorative result. Still further, sub-threshold stimulation applied to a patient's somatosensory cortex can alleviate pain without inducing paresthesia, which is a sensation of numbness or tingling.

For purposes of this invention, beneficial or desired clinical results include, but are not limited to, alleviation of symptoms, improvement of symptoms, diminishment of extent of disease, stabilized (i.e., not worsening) state of disease, delay or slowing of disease progression, amelioration or palliation of the disease state, and remission (whether partial or total), whether objective or subjective. The improvement is any observable or measurable improvement. Thus, one of skill in the art realizes that a treatment may improve the patient condition, but may not be a complete cure of the condition or disease.

In certain embodiments, in connection with improvement in one or more of the above or other neurological disorders, the electrical stimulation may have a "brightening" effect on the person such that the person looks better, pain-free, feels better, moves better, thinks better, and otherwise experiences an overall improvement in quality of life.

The present invention relates to methods of affecting pain (e.g., chronic pain) to regulate, prevent, treat, alleviate the symptoms of and/or reduce the effects of pain. Although not wishing to be bound to any particular definition or characterization, chronic pain can generally be characterized as being nociceptive or non-nociceptive pain. Nociceptive pain, also referred to as somatic pain, involves direct activation of the nociceptors, such as mechanical, chemical, and thermal receptors, found in various tissues, such as bone, muscle, vessels, viscera, and cutaneous and connective tissue. The afferent somatosensory pathways are thought to be intact in nociceptive pain and examples of such pain include cancer pain from bone or tissue invasion, non-cancer pain secondary to degenerative bone and joint disease or osteoarthritis, and failed back surgery. The foregoing examples of nociceptive pain are in no way limiting and the methods of the present invention encompass methods of affecting all types of nociceptive pain.

Non-nociceptive pain, also referred to as neuropathic pain, or deafferentation pain, occurs in the absence of activation of peripheral nociceptors. Non-nociceptive pain often results from injury or dysfunction of the central or peripheral nervous system. Such damage may occur anywhere along the neuroaxis and includes thalamic injury or syndromes (also referred to as central pain, supraspinal central pain, or post-stroke pain); stroke; traumatic or iatrogenic trigeminal (trigeminal neuropathic) brain or spinal cord injuries; phantom limb or stump pain; postherpetic neuralgia; anesthesia dolorosa; brachial plexus avulsion; complex regional pain syndrome I and II; postcordotomy dysesthesia; and various peripheral neuropathies. The foregoing examples of non-nociceptive pain are in no way limiting and the methods of the present invention encompass methods of affecting all types of non-nociceptive pain.

In certain embodiments, stimulation of the target brain tissue may be provided to effectively treat pain, for example chronic pain, acute pain, or subacute pain, deafferentation pain, phantom pain, or any other type of sensory input that is related to pain or any type of altered sensory input or altered sensory perception.

Chronic pain is difficult to treat. After development of the adult somatotopic representation, any alteration of the normal sensory input (either increase or decrease) leads to a reorganization of the entire somatosensory tract. This occurs daily throughout life under influence of environmental stimuli (Kandel, 1991; Yuste and Sur, 1999). Thus, any type of event in the person's life can result in alterations in this reorganization. For example, phantom pain and phantom sensations are associated with somatosensory cortex reorganization (Flor, 2003; Flor et al., 1995; Peyron et al., 2000), such that the cortical area originally corresponding to the amputated limb is taken over by sensory input from adjacent areas on Penfield's somatosensory homunculus (Pons et al., 1991). Furthermore magnetoecephalographic studies have shown a clear correlation between the amount of phantom pain and the extend of cortical reorganization (Flor et al., 1995).

In the somatosensory system, this reorganization seems to occur in two phases (Pons et al., 1991; Doetsch et al., 1996). Peripherally induced and maintained reorganization is initiated immediately after injury or training (Doetsch et al., 1996; Wiech et al., 2000). This first phase encompasses minutes to weeks and leads to axonal growth and synaptic sprouting. If maintained by peripheral input in a second phase permanent cortical, thalamothalamic or corticothalamic connections occur (Pons et al., 1991, Wieh et al., 2000) leading to intractable phantom limb pain. Changes in peripheral input afterwards do not affect the changes of the second phase (Wiech et al., 2000). This explains why the phantom pain becomes very difficult to treat once it exists for more than 6 months (Ramachandran and Hirstein, 1998).

Thus, the stimulation system and method used in the present alters or modulates this cortical reorganization to treat pain. The present invention utilizes techniques similar to the ones described in U.S. application Ser. No. 10/993,888, which is incorporated herein by reference in its entirety, as well as the techniques described in De Ridder et al., 2004. The technique involves mapping the brain mapping using standard functional neuroimaging techniques such as PET scan, fMRI or MSI to determine a target area, for example, the area of the brain possessing reorganization. Once target area or area of reorganization is determined, then an electrode, for example a cortex lead, can be implanted extradurally in communication with the target area.

Still further, in certain embodiments, stimulation of a target brain tissue site may be provided to effectively treat fibromyalgia or other diffuse pain in any one or more regions of the body.

In certain embodiments, stimulation of the target brain tissue site may effectively treat one or more neurological disorder associated with traumatic brain injury (TBI). Physiological conditions associated with TBI that may be treated effectively through stimulation of a brain tissue site include, for example, intractable localized, diffuse, or other pain in the head, neck, shoulders, upper extremities, or low back, fibromyalgia or other diffuse pain in one or more regions of the body, or other pain symptoms. Instead or in addition to such physiological conditions, psychological and other conditions associated with TBI that may be treated effectively through stimulation of the target brain tissue include, for example, intractable nausea (e.g., from gastroparesis), sleep disorders, chronic fatigue, behavioral modifications (e.g., lassitude, reduced motivation, depression, emotional distress, irritability, aggression, anxiety, erratic mood swings, personality changes, and loss of enjoyment), sexual dysfunction, and other conditions. Instead or in addition to physiological, psychological, and other conditions such as those described above, conditions associated with TBI that may be treated effectively through stimulation of the target brain tissue include decreased cognitive functioning in the form of, for example, impaired memory (e.g., short-term memory, visual memory, and auditory memory), reduced attention and concentration, and reduced information processing capacity (e.g., learning capacity, ability to process complex information, ability to operate simultaneously on different information, ability to rapidly shift attention, ability to plan and sequence, visuomotor capability, auditory language comprehension, and verbal fluency).

V. Programming of the Stimulation System

During the operation of stimulation system 10 according to a particular set of stimulation parameters, the efficacy of the stimulation associated with the particular set of stimulation parameters may decrease over time due to neuroplasticity of the brain. Neuroplasticity refers to the ability of the brain to dynamically reorganize itself in response to certain stimuli to form new neural connections. This allows the neurons in the brain to compensate for injury or disease and adjust their activity in response to new situations or changes in their environment. With respect to electrical stimulation, the reduction in efficacy due to neuroplasticity can occur after just a few weeks of treatment. In order to regain the same efficacy, a new set of efficacious electrical stimulation parameters must be determined, the new set of parameters must be entered into the system, and the system is again used to electrically stimulate the brain according to the new set of parameters to continue to treat the condition. This may result in the additional time and expense associated with a return visit to the treating physician for determining and entering the new set of parameters. Especially where treatment is to continue over a relatively long period of time, such as months or years, this additional time and expense poses a significant drawback.

Thus, in certain embodiments, in addition to providing therapeutic electrical stimulation to the brain for treating the condition in the person's body, stimulation system 10 may be capable of applying additional electrical stimulation to the brain to reduce neuroplasticity effects associated with the therapeutic electrical stimulation as described in U.S. application Ser. No. 10,994,008 entitled "Electrical Stimulation System, lead and Method Providing Reduced Neuroplasticity Effects," which is incorporated herein by reference in its entirety.

In one embodiment, the nature of the neuroplasticity reducing electrical stimulation may be varied more or less continually, in a predetermined or randomized manner, to prevent, delay, or otherwise reduce the ability of the brain to adapt to the neuroplasticity reducing electrical stimulation and dynamically reorganize itself accordingly. In a more particular embodiment, the neuroplasticity reducing electrical stimulation may be randomized or otherwise varied about the therapeutic electrical stimulation to achieve this result. In essence, the randomized or otherwise varied neuroplasticity reducing electrical stimulation makes it more difficult for the brain to dynamically reorganize itself to overcome the effects of the therapeutic electrical stimulation.

In certain other embodiments, stimulation system 10 may similarly be capable of applying additional electrical stimulation to the brain to enhance, rather than reduce, neuroplasticity effects associated with the therapeutic electrical stimulation. In one embodiment, the nature of the neuroplasticity enhancing electrical stimulation may controlled in a predetermined non-randomized manner to promote, accelerate, or otherwise enhance the ability of the brain to adapt to the neuroplasticity enhancing electrical stimulation and dynamically reorganize itself accordingly. In essence, the predetermined non-randomized neuroplasticity enhancing electrical stimulation facilitates the brain dynamically reorganizing itself in response to the therapeutic electrical stimulation. It should be understood that techniques analogous to some or all of those discussed below for reducing neuroplasticity effects may be employed for enhancing neuroplasticity effects.

Figure 6:
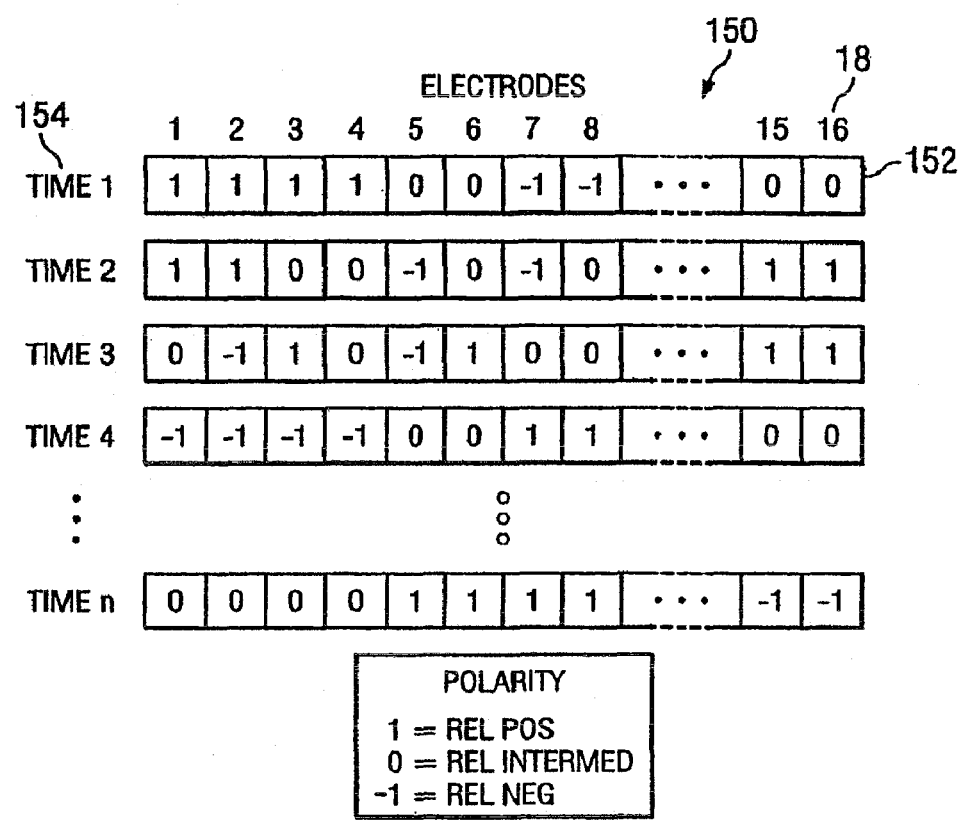
FIG. 6 illustrates an example stimulation set.

FIG. 6 illustrates an example stimulation set 150. One or more stimulation sets 150 may be provided, each stimulation set 150 specifying a number of stimulation parameters for the stimulation set 150. For example, as described more fully below with reference to FIGS. 7-8, multiple stimulation sets 150 may be executed in an appropriate sequence according to a pre-programmed or randomized stimulation program.

Stimulation parameters for a stimulation set 150 may include an amplitude or intensity, a frequency, phase information, and a pulse width for each of a series of stimulation pulses that electrodes 18 are to deliver to the target nerve tissue during a time interval during which stimulation set 150 is executed, along with a polarity 152 for each electrode 18 within each stimulation pulse. In general, electric fields are generated between adjacent electrodes 18 having different polarities 152 to deliver electrical stimulation pulses to nerve tissue. Stimulation parameters may also include a pulse shape, for example, biphasic cathode first, biphasic anode first, or any other suitable pulse shape.

For reducing neuroplasticity effects associated with therapeutic electrical stimulation, one or more stimulation parameters for a stimulation set 150 may be randomized or otherwise varied in any suitable manner within the time interval in which stimulation set 150 is executed, spanning one or more stimulation pulses within each stimulation pulse. For example, instead of or in addition to randomizing or otherwise varying polarities 152 for electrodes 18 as described below, the amplitude or intensity, frequency, phase information, and pulse width may be randomized or otherwise varied within predetermined ranges, singly or in any suitable combination, within each stimulation pulse. As another example, instead of or in addition to randomizing or otherwise varying polarities 152 for electrodes 18 over multiple stimulation pulses as described more fully below, the amplitude or intensity, frequency, phase information, and pulse width may be randomized or otherwise varied within predetermined ranges, singly or in any suitable combination, over multiple stimulation pulses, where the combination of stimulation parameters is substantially constant within each stimulation pulse but different for successive stimulation pulses. Such randomization or other variation of stimulation parameters for a stimulation set 150 reduces the ability of the brain to adapt to the neuroplasticity reducing electrical stimulation and dynamically reorganize itself to overcome the effects of the neuroplasticity reducing stimulation.

The polarity for an electrode 18 at a time 154 beginning a corresponding stimulation pulse or sub-interval within a stimulation pulse may be a relatively positive polarity 152, a relatively negative polarity 152, or an intermediate polarity 152 between the relatively positive polarity 152 and relatively negative polarity 152. For example, the relatively positive polarity 152 may involve a positive voltage, the relatively negative polarity 152 may involve a negative voltage, and the relatively intermediate polarity 152 may involve a zero voltage (i.e. "high impedance"). As another example, the relatively positive polarity 152 may involve a first negative voltage, the relatively negative polarity 152 may involve a second negative voltage more negative than the first negative voltage, and the relatively intermediate polarity 152 may involve a negative voltage between the first and second negative voltages. The availability of three distinct polarities 152 for an electrode 18 may be referred to as "tri-state" electrode operation. The polarity 152 for each electrode 18 may change for each of the sequence of times 154 corresponding to stimulation pulses or to sub-intervals within a stimulation pulse according to the stimulation parameters specified for the stimulation set 150. For example, as is illustrated in FIG. 6 for an example stimulation set 150 for a lead 14 with sixteen electrodes 18, the polarities 152 of the sixteen electrodes 18 may change for each of the sequence of times 154. In the example of FIG. 6, a relatively positive polarity 152 is represented using a "1," a relatively intermediate polarity 152 is represented using a "0," and a relatively negative polarity 152 is represented using a "−1," although any suitable values or other representations may be used.

Where appropriate, the polarity 152 for each electrode 18 may change in a predetermined or randomized manner, randomized changes possibly being more effective with respect to any neuroplasticity reducing stimulation for reasons described above.

Where stimulation system 10 provides, in addition to therapeutic electrical stimulation, electrical stimulation to reduce neuroplasticity effects associated with the therapeutic electrical stimulation, each stimulation pulse or sub-interval within a stimulation pulse may be particular to the stimulation being provided; that is, either to therapeutic electrical stimulation or to neuroplasticity reducing electrical stimulation. For example, one or more stimulation pulses or sub-intervals may be designed to provide therapeutic electrical stimulation and one or more other stimulation pulses or sub-intervals may be designed to reduce neuroplasticity effects. In this case, the therapeutic stimulation pulses or sub-intervals and neuroplasticity reducing stimulation pulses or sub-intervals may be arranged temporally in any suitable manner. A therapeutic stimulation pulse or sub-interval may be separated from a successive therapeutic stimulation pulse or sub-interval by any number of neuroplasticity reducing stimulation pulses or sub-intervals and this number may be the same between each pair of therapeutic stimulation pulses or sub-intervals or may vary between each pair of therapeutic stimulation pulses or sub-intervals in a predetermined or randomized manner. As another example, one or more stimulation pulses or sub-intervals may be designed to concurrently provide both therapeutic and neuroplasticity reducing electrical stimulation.

Similarly, where stimulation system 10 provides, in addition to therapeutic electrical stimulation, electrical stimulation to reduce neuroplasticity effects associated with the therapeutic electrical stimulation, each stimulation set 150 may be particular to either the therapeutic electrical stimulation or the neuroplasticity reducing electrical stimulation. For example, one or more stimulation sets 150 may be designed to provide therapeutic electrical stimulation and one or more other stimulation sets 150 may be designed to reduce neuroplasticity effects. In this case, the therapeutic stimulation sets 150 and neuroplasticity reducing stimulation sets 150 may be arranged temporally in any suitable manner. A therapeutic stimulation set 150 may be separated from a successive therapeutic stimulation set 150 by any number of neuroplasticity reducing stimulation sets 150 and this number may be the same between each pair of therapeutic stimulation sets 150 or may vary between each pair of therapeutic stimulation sets 150 in a predetermined or randomized manner. As another example, one or more stimulation sets 150 may be designed to concurrently provide both therapeutic and neuroplasticity reducing electrical stimulation.

In addition, the amplitude or intensity, frequency, phase information, or pulse width for a stimulation set 150 may be particular to the stimulation being provided. For example, therapeutic electrical stimulation may be provided using higher amplitude electrical energy than is used for neuroplasticity reducing electrical stimulation. In this case, the neuroplasticity reducing electrical stimulation may be below the therapeutic target threshold stimulation (i.e. below the threshold where therapeutic electrical stimulation is provided to adjust the level of activity in the target nerve tissue in the person's brain to treat the condition in the person's body). Alternatively, neuroplasticity reducing electrical stimulation may be provided using the same or a higher amplitude electrical energy than is used for therapeutic electrical stimulation (i.e. at or above the threshold where therapeutic electrical stimulation is provided to adjust the level of activity in the target nerve tissue in the person's brain to treat the condition in the person's body). In this case, the neuroplasticity reducing electrical stimulation's primary purpose is not to produce a therapeutic effect, but rather to reduce neuroplasticity. In this manner, the neuroplasticity reducing electrical stimulation could have both a therapeutic and neuroplasticity reducing effect.

Figure 8:
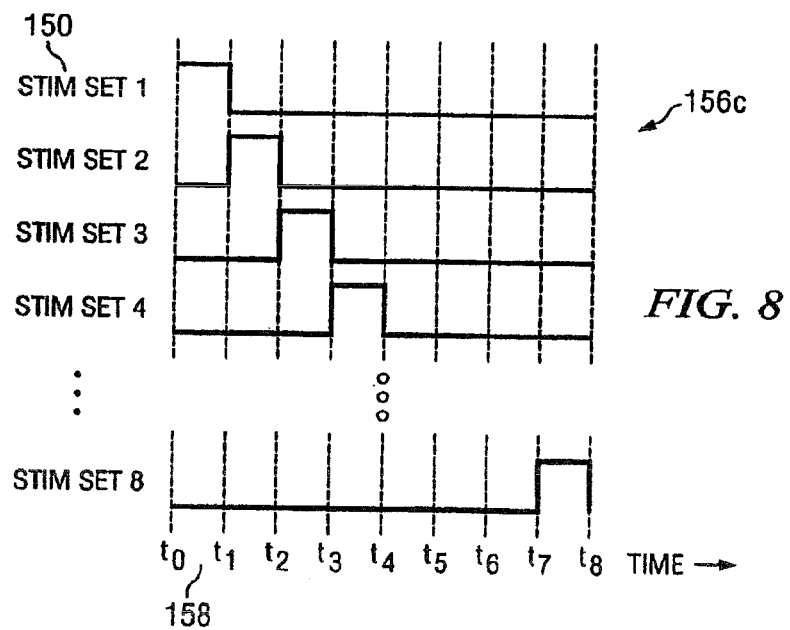
FIG. 8 illustrates example execution of a sequence of stimulation sets within an example stimulation program.
Figure 2A:
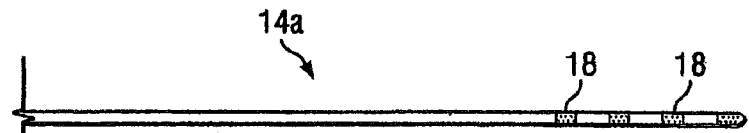
FIGS. 2A-2I illustrate example electrical stimulation leads that may be used to electrically stimulate target nerve tissue in the brain identified through imaging of the brain to treat a condition in the body and, in certain embodiments, provide reduced or enhanced neuroplasticity effects in the brain.
Figure 2B:
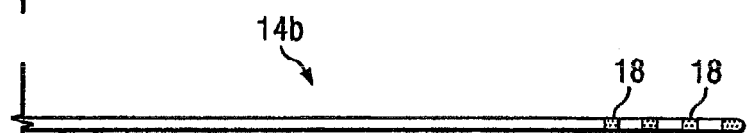
Figure 2C:
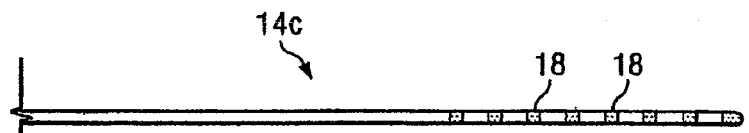
Figure 2D:
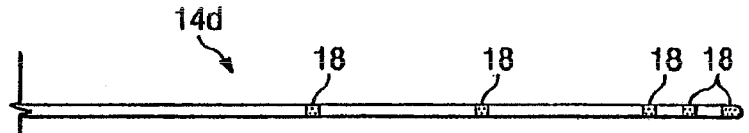
Figure 2E:
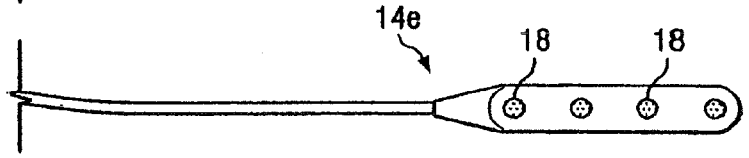
Figure 2F:
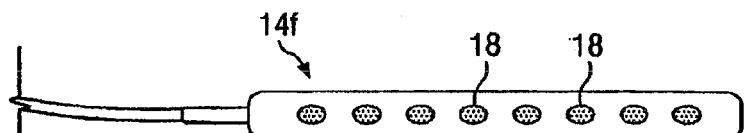
Figure 2G:
Figure 2H:
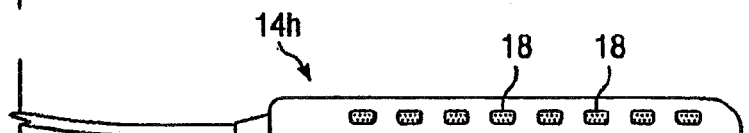
Figure 2I:
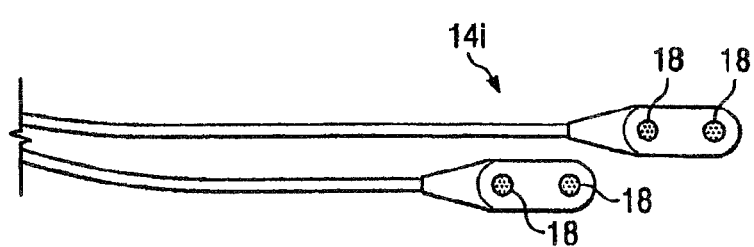
Figure 7:
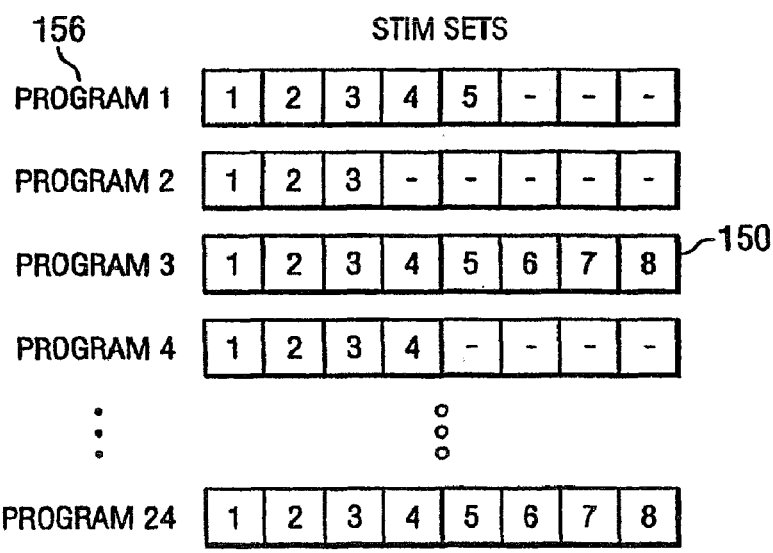
FIG. 7 illustrates a number of example stimulation programs, each of which includes a number of stimulation sets.

FIG. 7 illustrates a number of example stimulation programs 156, each including a number of stimulation sets 150. One or more simulation programs 156 may be set up to reduce neuroplasticity effects associated with therapeutic electrical stimulation of the brain. As described above, each stimulation set 150 specifies a number of stimulation parameters for the stimulation set 150. In one embodiment, within each stimulation program 156, stimulation system 10 consecutively executes the sequence of one or more stimulation sets 150 associated with stimulation program 156. The sequence may be executed only once, repeated a specified number of times, or repeated an unspecified number of times within a specified time period. For example, as is illustrated in FIG. 8 for the third example stimulation program 156c including eight stimulation sets 150, each of the eight stimulation sets 150 is consecutively executed in sequence. Although the time intervals 158 (t1-t0, t2-t1, etc.) during which the stimulation sets 150 are executed are shown as being equal, the present invention contemplates a particular stimulation set 150 being executed over a different time interval 158 than one or more other stimulation sets 150 according to particular needs. One or more stimulation sets 150 within at least one stimulation program 156 may be set up to provide reduced neuroplasticity effects associated with therapeutic electrical stimulation of the brain.

Although stimulation system 10 is illustrated by way of example as accommodating up to twenty-four stimulation programs 156 each including up to eight stimulation sets 150, the present invention contemplates any appropriate number of stimulation programs 156 each including any appropriate number of stimulation sets 150. For example, in a very simple case, a single stimulation program 156 may include a single stimulation set 150, whereas in a very complex case more than twenty-four stimulation programs 156 may each include more than eight stimulation sets 150.

In one embodiment, stimulation system 10 executes only a single stimulation program 156 in response to user selection of that stimulation program for execution. In another embodiment, during a stimulation period, stimulation system 10 executes a sequence of pre-programmed stimulation programs 156 for each lead 14 until the stimulation period ends. Depending on the length of the stimulation period and the time required to execute a sequence of stimulation programs 156, the sequence may be executed one or more times. For example, the stimulation period may be defined in terms of a predetermined number of cycles each involving a single execution of the sequence of stimulation programs 156, the sequence of stimulation programs 156 being executed until the predetermined number of cycles has been completed. As another example, the stimulation period may be defined in terms of time, the sequence of stimulation programs 156 being executed until a predetermined time interval has elapsed or the patient or another user manually ends the stimulation period. Although a sequence of stimulation programs 156 is described, the present invention contemplates a single stimulation program being executed one or more times during a stimulation period according to particular needs. Furthermore, the present invention contemplates each stimulation program 156 being executed substantially immediately after execution of a previous stimulation program 156 or being executed after a suitable time interval has elapsed since completion of the previous stimulation program 156. Where stimulation system 10 includes multiple leads 14, stimulation programs 156 for a particular lead 14 may be executed substantially simultaneously as stimulation programs 156 for one or more other leads 14, may be alternated with stimulation programs 156 for one or more other leads 14, or may be arranged in any other suitable manner with respect to stimulation programs 156 for one or more other leads 14.

Where stimulation system 10 provides, in addition to therapeutic electrical stimulation, electrical stimulation to reduce neuroplasticity effects, each stimulation program 156 may be particular to either the therapeutic electrical stimulation or the neuroplasticity reducing electrical stimulation. For example, one or more stimulation programs 156 may be designed to provide therapeutic electrical stimulation and one or more other stimulation programs 156 may be designed to reduce neuroplasticity effects. In this case, the therapeutic stimulation programs 156 and the neuroplasticity reducing stimulation programs 156 may be arranged temporally in any manner. A therapeutic stimulation program 156 may be separated from a successive therapeutic stimulation program 156 by any number of neuroplasticity reducing stimulation programs 156 and this number may be the same between each pair of therapeutic stimulation programs 156 or may vary between each pair of therapeutic stimulation programs 156 in a predetermined or randomized manner. As another example, one or more stimulation programs 156 may be set up to concurrently provide both therapeutic and neuroplasticity reducing electrical stimulation.

In general, each stimulation program 156 may, but need not necessarily, be set up for electrical stimulation of different target nerve tissue in a person's brain. As an example, where therapeutic electrical stimulation of target nerve tissue in a particular region 38 of the brain is desired, one or more stimulation programs 156 may be set up for therapeutic electrical stimulation of the target nerve tissue in the particular region 38 and one or more other stimulation programs 156 may be set up for electrical stimulation of the same target nerve tissue in the particular region 38 to reduce neuroplasticity effects associated with the therapeutic electrical stimulation. As another example, one or more stimulation programs 156 may be set up for therapeutic electrical stimulation of target nerve tissue in a particular region 38 of the brain and one or more other stimulation programs 156 may be set up for electrical stimulation of different nerve tissue in either the same region 38 or in a different region 38 of the brain to reduce neuroplasticity effects associated with the therapeutic electrical stimulation.

As described above, in one embodiment, the nature of any neuroplasticity reducing electrical stimulation may be varied more or less continually, whether in a predetermined or randomized manner, to reduce, prevent, delay, enhance, promote, or otherwise control the ability of the brain to adapt to the neuroplasticity reducing electrical stimulation and dynamically reorganize itself accordingly. In a more particular embodiment, where the neuroplasticity reducing electrical stimulation is provided concurrently with therapeutic electrical stimulation, the neuroplasticity reducing electrical stimulation may be randomized or otherwise varied about the therapeutic electrical stimulation to achieve this result. In essence, the randomized or otherwise varied neuroplasticity reducing electrical stimulation makes it more difficult for the brain to dynamically reorganize itself to overcome the effects of the therapeutic electrical stimulation.

The present invention contemplates any suitable circuitry within stimulation source 12 for generating and transmitting electrical stimulation pulses for electrically stimulating target nerve tissue in a person's brain to treat a condition in the person's body and, where appropriate, to reduce, enhance, or otherwise treat neuroplasticity effects in the person's brain, whether separate from or concurrently with the therapeutic electrical stimulation. Example circuitry that may be used is illustrated and described in U.S. Pat. No. 6,609,031 B1, which is hereby incorporated by reference herein as if fully illustrated and described herein.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Treatment of Deafferentation Pain

In general, patients with intractable deafferentation pain were selected for neuronavigated transcranial magnetic stimulation (TMS) of the somatosensory cortex.

Prior to TMS a fMRI of the somatosensory cortex was performed demonstrating the area of reorganization. A fMRI was performed, applying tactile stimulation at the deafferented area, inducing hyperalgesia/allodynia. The FMRI demonstrated an area of hyperactivity on the contralateral primary/secondary somatosensory cortex.

TMS was used to verify the potential benefit of electrical stimulation of the somatosensory cortex. Subsequently a TMS was performed by means of fMRI based neuronavigation (Treon, Medtronic) at 90% motor threshold (MT). If pain suppression was obtained, placebo stimulation at the same site was performed. Stimulation at 110% MT was also tested to exclude motor cortex involvement. The pain suppression obtained by TMS was transient.

Five of the 8 patients had beneficial effect with TMS and underwent an implantation of a cortical electrode on the somatosensory cortex. Continuous pain suppression was obtained by implantation of an epidural electrode (Lamitrode 44, ANS Inc. Plano, Tex.) on the area of cortical reorganization as located by fMRI based neuronavigation. In 3 of 5 patients this treatment was highly beneficial, in 1 partly successful due to multiple recurrences, requiring reprogrammation, in 1 pain recurs after initial suppression.

Four out of five patients remained pain free without paresthesias induced by the cortical stimulation. In one of these patients multiple reprogrammations were required for continuing pain suppression. Initially 4-7 Hz stimulation was used at low amplitudes (0.5-2 mA). Stimulation at higher frequencies and amplitudes induced pain in the area of deafferentation. In one patients pain recurred after initial suppression.

Thus, stimulation of the somatosensory cortex stimulation can be used for pain control in patients presenting with intractable deafferentation pain.

Example 2

Treatment of Pain

Patient History

A 53 year old woman presented with a 10 year history of persistent lancinating pain in the right supraorbital region. The pain arose a few weeks after a surgical excision of basocellular carcinoma on the right forehead. Initially she suffered a normal post operative pain progressively evolving to a constant, sharp lancinating pain. Multiple surgical procedures followed with aggravation of the symptoms.

Except for the pain she also developed a sensation of her right eye being located on her right maxillary arc. Despite a normal vision as demonstrated by an extensive neuro-ophthalmological work-up, the phantom sensation often induced a misperception of the position of surrounding objects causing her to run into obstacles ipsilateral to the phantom sensation.

Clinical Examination

A hyperalgesia and a loss of sensation of temperature and vibration in the right VI dermatoma were noted. Tactile stimulation of the medial cornea and upper eyelashes of the right eye were sensed at the phantom eye at the right maxillary arc. Tactile stimulation of the medial cornea and medial upper and lower eyelashes of the phantom eye were sensed at the corresponding areas at the ipsilateral eye. Phantom corneal reflex was not elicited. Further clinical exams were normal.

Figure 9A:
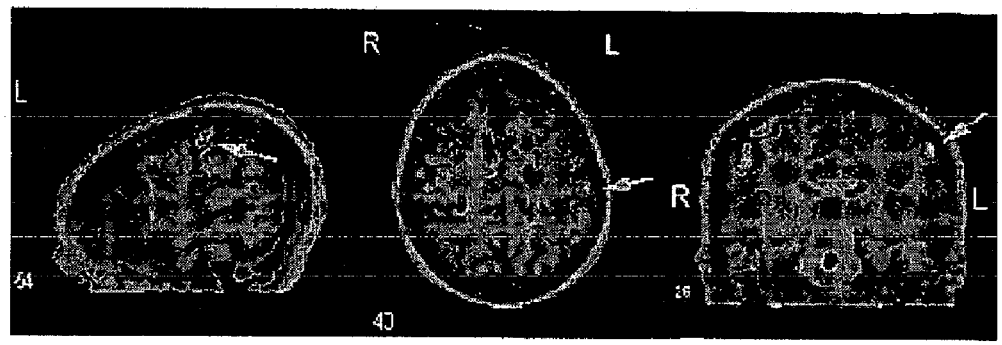
FIG. 9A and FIG. 9B illustrate fMRI activity (thresholded at T>7) overlayed on saggital, transverse and coronal slices (FIG. 9A) as well as a surface reconstruction of the patient's brain (FIG. 9B). Arrow indicates area of V1 pain sensation, located within the left postcentral gyrus. Other areas of activity were found in left primary sensorymotor cortex, supplementary motor area, right cerebellum and are related to the motor activity of the left hand and arm rubbing the right V1 skin area.
Figure 9B:
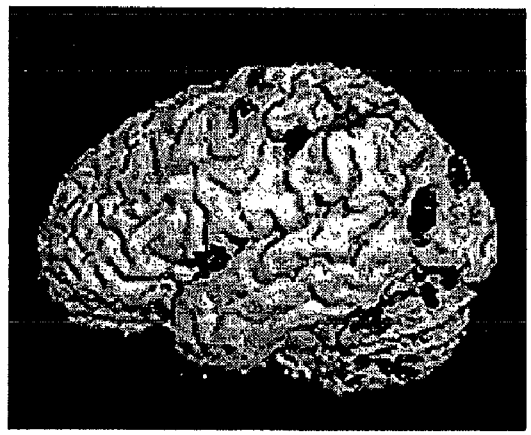

Functional Magnetic Resonance Imaging (fMRI)

fMRI was performed on a 3T MR system using the blood oxygen level dependend (BOLD) method and consisted of acquisition of whole brain FFE-EPI images (resolution of 3.times.3.times.4 mm, TE/TR=33/3000 ms) as well as high resolution Ti weighted anatomical images. The stimulation paradigm was a blocked fMRI design alternating 30 s epochs of sensory stimulation (the patient rubbed the painful right V1 skin area using her left hand) with 30 s epochs of non-stimulation (rest). Statistical comparison of brain activity during skin stimulation to rest resulted in a significant area of activity in the left postcentral gyrus corresponding to the area of perception of pain located within the left primary sensory cortex (FIG. 9). Other areas of activity were found in left primary sensorimotor cortex, supplementary motor area, right cerebellum, and were related to the motor activity of the left hand and arm rubbing the right VI skin area.

Transcranial Magnetic Stimulation (TMS)

Transcranial magnetic stimulation was performed with a Super Rapid magnetic stimulator (Magstim Inc, Wales, UK.) allowing stimulation in a range of 1 to 50 Hz. Magnetic stimulation was performed after neuronavigation guided localization (Stealth, Sofamor Danek, Colo., USA) of the area of cortical reorganization based on the predefined area on the FMRI. Several series of stimulation were applied with different frequencies and intensities on target and adjacent areas.

The transcranial magnetic stimulation (TMS) caused a maximum reduction of 80% of the supraorbital pain and a complete disappearance of the phantom sensation.

The suppression of the pain was obtained immediately after starting the TMS and had a residual effect whereas the phantom shifted back to its normal position after a longer period of stimulation.

Figure 10:
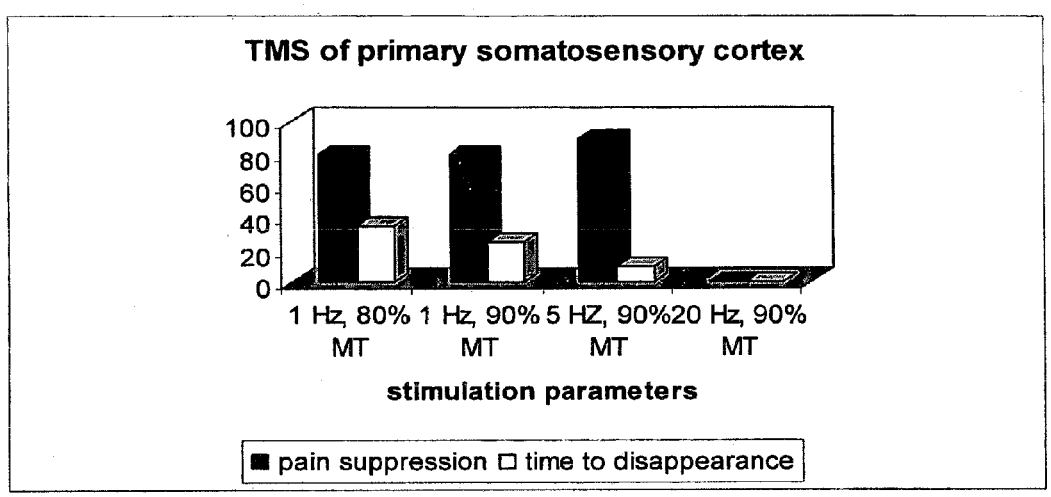
FIG. 10 shows that the amount of pain suppression is related to the stimulation frequency used. The same relation is seen for the time required for the phantom eye to disappear.

TMS on target (FIG. 9) using a rate of 1 pulse per second (pps) during 60 seconds at an intensity of 90% motor threshold (MT) caused an immediate pain reduction of 80% and complete disappearance of the phantom sensation after 25 seconds of stimulation. The same pain relief was obtained with TMS at a rate of 5 pps and 90% MT but the phantom eye shifted back in 10 seconds. TMS with 10 consecutive 500 ms bursts at 20 pps at 90% MT had no beneficial effect on the pain or the phantom. Lowering the output to 80% MT at a rate of 1 pps still induced an 80% pain reduction but the phantom progressively disappeared after 35 seconds of stimulation. Sham stimulation had no effect. TMS at 110% MT did not elicit any motor activity. (FIG. 10)

Consecutively an epidural octopolar electrode (Lamitrode 44, Advanced Neuromodulation Systems Inc, Tx, USA.) was implanted for electrical stimulation of the somatosensory cortex. The electrode was located at the predefined target using FMRI based frameless stereotaxic guidance. The leads of the electrodes were tunneled subcutaneously to the abdominal wall and connected to the internal pulse generator (IPG) (Genesis, Advanced Neuromodulation Systems Inc. Tx, USA) and implanted in a subcutaneous pocket. The postoperative course was uneventful.

After recovery from the surgery the patient felt the same pain and phantom sensation as preoperatively. On the first postoperative day the IPG was activated and a complete suppression of pain and a complete disappearance of the phantom eye was obtained. Stimulation parameters were set in an alternating 30 seconds ON and 60 seconds OFF mode with 50 .mu.sec pulse width, 4 pps at 1.0 mA. Stimulating with these parameters induced paresthesias in the right supraorbital region. Lowering the intensity to 0.3 mA had a similar effect on the pain and phantom but without any paresthesias. Furthermore the patient had no problem in determining the exact position of surrounding objects after stimulation parameters were set.

Patient was discharged 4 days after surgery completely free of pain and phantom sensation and remained as such after 12 months follow-up.

Figure 11A:
FIGS. 11A-11C show site of stimulation.
Figure 11B:
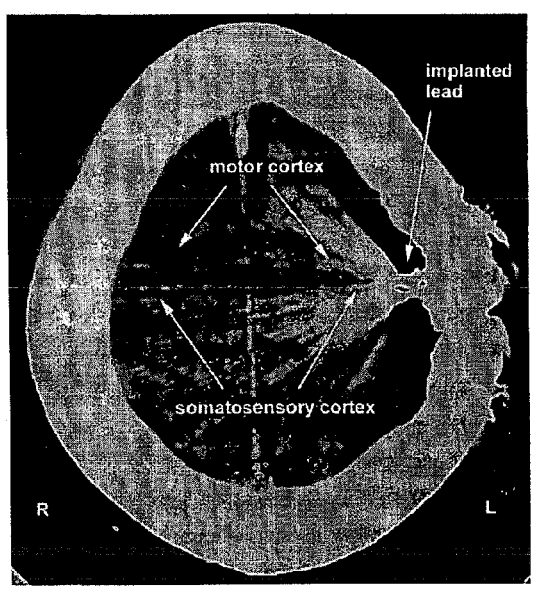
Figure 11C:
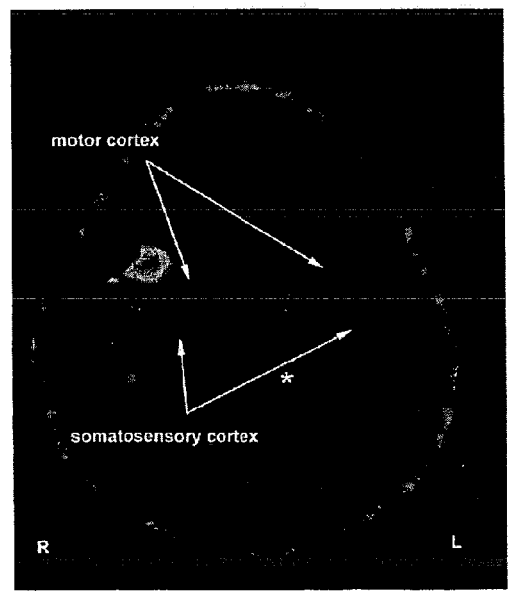

Postoperative images revealed a correct position of the lead on the somatosensory cortex and not on the motor cortex (FIGS. 11A and B). Thus, somatosensory cortex stimulation can be used for anaesthesia dolorosa and phantom sensation.

REFERENCES CITED

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

Brown J A, Barbaro N M. Motor cortex stimulation for central and neuropathic pain: current status. Pain 2003 August; 104 (3): 431-435

Bruehlmeier M, Dietz V, Leenders K L, Roelcke U, Missimer J, Curt A. How does the human brain deal with a spinal cord injury? Eur J Neurosci. 1998 December; 10(12): 3918-22

Condes-Lara M, Barrios F A, Romo J R, Rojas R, Salgado P, Sanchez-Cortazar J. Brain somatic representation of phantom and intact limb: a FMRI study case report. Eur J Pain. 2000; 4(3):239-45.

De Ridder D, De Mulder G, Walsh V, Muggleton N, Sunaert S, Moller A. Magnetic and electrical stimulation of the auditory cortex for intractable tinnitus. Case report. J Neurosurg 2004 March; 100(3): 560-564

Doetsch G S, Harisson T A, MacDonald A C, Litaker M S. Short term plasticity in primary somatosensory cortex of the rat: rapid changes in magnitudes and latencies of neuronal responses following digit denervation. Exp Brain Res 1996 December; 112: 505-512

Flor H, Elbert T, Knecht S, Wienbruch C, Pantev C, Birbaumer N, Larbig W, Taub E. Phantom limb pain as a perceptual correlate of cortical reorganization following arm amputation. Nature 1995 June; 8: 375 (6531): 482-484

Flor H. Cortical reorganization and chronic pain: implications for rehabilitation. J. Rehabil Med. 2003 May; 41 Suppl: 66-72

Halbert J, Crotty M, Cameron I D. Evidence for the optimal management of acute and chronic phantom pain: a systematic review. Clin J Pain. 2002 March-April; 18(2): 84-92

Jastreboff P J. Phantom auditory perception (tinnitus): Mechanisms of generation and perception. Neurosci Res. 1990 August; 8(4): 221-254

Kaas J H, Merzenich M M, Killackey H P. The reorganization of somatosensory cortex following peripheral nerve damage in adult and developing mammals. Annu Rev Neurosci. 1983; 6: 325-56

Katayama Y. Yamamoto T, Kobayashi K, Kasai M, Oshima H, Fukaya C. Motor cortex stimulation for phantom limb pain: comprehensive therapy with spinal cord and thalamic stimulation. Stereotact Funct Neurosurg. 2001; 77(1-4): 159-62

Kandel E R. Cellular mechanisms of hearing and the biological basis of individuality. Principles of Neural Science, 3rd ed, Appleton & Lange Norwalk, Conn.: 1009-1031, 1991

Knecht S, Henningsen H, Hohling C, Elbert T, Flor H, Pantev C. Plasticity of plasticity? Changes in the pattern of perceptual correlates of reorganization after amputation. Brain 1998 April; 121(Pt4): 717-724

Kumar K, Toth C, Nath R K. Deep brain stimulation for intractable pain: a 15 year experience. Neurosurgery 1997 April; 40(4):736-746

Lende R, Kirsch W, Druckman R. Relief of facial pain after combined removal of precentral and postcentral cortex. J Neurosurg 1971; 34: 537-543

Lenz F, Kwan H, Dostrovsky J O, Tasker R R. Characteristics of the bursting pattern of action potentials that occurs in the thalamus of patients with central pain. Brain Res. 1989 September; 496 (1-2): 357-360

Levy R M, Lamb S, Adams J E. Treatment of chronic pain by deep brain stimulation: long term follow-up and review of the literature. Neurosurgery 1987 December; 21(6): 885-893

Lotze M, Flor H, Grodd W, Larbig W, Birbaumer N. Phantom movements and pain. An f MRI study in upper limb amputees. Brain 2001 November; 124 (Pt11): 2268-2277

Merzenich M M, Nelson R J, Stryker M P, Cynader M S, Schoppmann A, Zook J M. Somatosensory cortical map changes following digit amputation in adult monkeys. J Comp Neurol. 1984 Apr. 20; 224(4):591-605.

Moller A R. Similarities between chronic pain and tinnitus. AM J Otol. 1997 September; 18: 577-585

Moller A R: The role of neural plasticity in disorders of the nervous system. Cambridge University Press, In press Nguyen J P, Keravel Y, Feve A, Uchiyama T, Cesaro P, Le Guerinel C, Pollin B. Treatment of deafferentation pain by chronic stimulation of the motor cortex. Report of a series of 20 cases. Acta Neurochir Suppl (Wien) 1997; 68: 54-60

Nikolajsen L, Jensen T S. Phantom limb pain. Br J Anaesth. 2001 July; 87(1): 107-16

Peyron R, Laurent B, Garcia-Larrea L. Functional imaging of brain responses to pain. A review and meta-analysis (2000). Neurophysiol Clin. 2000 October; 30(5): 263-88

Pons T P, Garraghty P E, Ommaya A K, Kaas J H, Taub E, Mishkin M. Massive cortical reorganization after sensory deafferentation in adult macaques. Science. 1991 Jun. 28; 252 (5014): 1857-1860

Ramachandran V S. Behavioral and magnetoencephalographic correlates of plasticity in the adult human brain. Proc. Natl. Acad. Sci. USA. 1993 Nov. 15; 90(22): 10413-20

Ramachandran V S, Hirstein W. The perception of phantom limbs. The D. O. Hebb lecture. Brain 1998 September 121(Pt9): 1603-1630

Rinaldi P C, Young R F, Albe-Fessard D, Chodakiewitz J. Spontaneous neuronal hyperactivity in the medial and intrlaminar thalamic nuclei of patients with deafferentation pain. J Neurosurg 1991 March; 74: 415-421

Sherman R A, Sherman C J, Parker L. Chronic phantom and stump pain among American veterans: results of a survey. Pain 1984 January; 18(1): 83-95

Theuvenet P J, Dunajski Z, Peters M J, Van Ree J M. Responses to median and tibial nerve stimulation in patients with chronic neuropathic pain. Brain Topogr 1999 Summer; 11 (4): 305-313

Tonndorf J. The analogy between tinnitus and pain: a suggestion for a physiological basis of chronic tinnitus. Hear Res 1987; 28 (2-3): 271-275

Tsubokawa T, Katayama Y, Yamamoto T, Hirayama T, Koyama S. Chronic motor cortex stimulation for the treatment of central pain. Acta Neurochir Suppl (Wien) 1991; 52: 137-139

Tsubokawa T, Katayama Y, Yamamoto T, Hirayama T, Koyama S. Treatment of thalamic pain by chronic motor cortex stimulation. Pacing Clin Electrophysiol 1991 January 14(1): 131-124

Weiss T, Miltner W H, Huonker R, Friedel R, Schmidt I, Taub E. Rapid functional plasticity of the somatosensory cortex after finger amputation. Exp Brain Res. 2000 September; 134(2): 199-203

Wiech K, Preissl H, Lutzenberges W, Kiefer R T, Topfner S, Haerle M, Schaller H G, Birbaumer N. Cortical reorganization after digit to hand replantation. J. Neurosurg 2000 November; 93(5): 876-883

Yuste R, Sur M. Development and plasticity of the cerebral cortex: from molecules to maps. I. Neurobiol 1999 October; 41(1): 1-6

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed:

1. A method of treating a neurological condition in a patient using electrical stimulation comprising:
    mapping a target cortical site on the cortex of a brain of the patient to be stimulated, wherein mapping comprises identifying an area of the cortex having altered neuronal activity such that the altered neuronal activity is an area of cortical reorganization, the identified area is the target cortical site;
    applying electromagnetic stimulation to the target cortical site via transcranial magnetic stimulation; and
    determining if electromagnetic stimulation of the target cortical site improved the patient's neurological condition;
    placing electrodes extradurally such that the electrodes are below the skull and on the dura over the patient's target cortical site if it is determined that transcranial magnetic stimulation improved the patient's neurological condition; and
    treating the neurological condition by generating electrical signals with a signal generator using the electrodes wherein the signal electrically stimulates the patient's cortex to treat the condition.

2. The method of claim 1, wherein the neurological condition is depression.

* * * * *